United States Patent [19]

Minagawa et al.

[11] Patent Number: 5,656,471
[45] Date of Patent: Aug. 12, 1997

[54] LACTATE OXIDASE WITH AN IMPROVED THERMAL STABILITY AND GENE OF THE SAME

[75] Inventors: Hirotaka Minagawa; Noriyuki Nakayama; Shinya Nakamoto, all of Tokyo, Japan

[73] Assignee: NEC Corporation, Tokyo, Japan

[21] Appl. No.: 625,876

[22] Filed: Apr. 1, 1996

[30] Foreign Application Priority Data

Mar. 30, 1995 [JP] Japan ........................... 7-095947
Jun. 13, 1995 [JP] Japan ........................... 7-146186

[51] Int. Cl.[6] ........................... C12N 9/04
[52] U.S. Cl. ................ 435/190; 435/252.3; 435/252.33; 435/252.8; 435/252.9; 435/320.1; 536/23.1; 536/23.2

[58] Field of Search ................ 435/190, 252.3, 435/252.33, 252.8, 252.9, 320.1; 536/23.2, 23.1

[56] References Cited

PUBLICATIONS

Minagawa et al. "Thermostabilization of lactate oxidase by random mutagenesis" Biotech. Lett. 17(9), 975–980 Sep. 1995.

*Primary Examiner*—Charles L. Patterson, Jr.
*Assistant Examiner*—Nashaat T. Nashed
*Attorney, Agent, or Firm*—Young & Thompson

[57] ABSTRACT

A lactate oxidase (LOD15, LOD1, LOD16) shows an enzymatic activity under a reaction represented by "L-lactate+oxygen→pyruvic acid+hydrogen peroxide". A DNA molecule comprises nucleotide sequences which code on expression for a lactate oxidase (LOD15, LOD1, LOD16).

3 Claims, 8 Drawing Sheets

```
5' ATGAATAACA ATGACATTGA ATATAATGCA CCTAGTGAAA TCAAGTACAT
3' TACTTATTGT TACTGTAACT TATATTACGT GGATCACTTT AGTTCATGTA

TGATGTTGTC AATACTTACG ACTTAGAAGA AGAAGCAAGT AAAGTGGTAC
   ACTACAACAG TTATGAATGC TGAATCTTCT TCTTCGTTCA TTTCACCATG

CACATGGTGG TTTTAACTAT ATTGCTGGTG CATCTGGTGA TGAGTGGACT
   GTGTACCACC AAAATTGATA TAACGACCAC GTAGACCACT ACTCACCTGA

AAACGCGCTA ATGACCGTGC TTGGAAACAT AAATTACTAT ACCCACGTCT
   TTTGCGCGAT TACTGGCACG AACCTTTGTA TTTAATGATA TGGGTGCAGA

AGCGCAAGAT GTTGAAGCGC CGATACAAG TACTGAAATT TTAGGTCATA
   TCGCGTTCTA CAACTTCGCG GCTATGTTC ATGACTTTAA AATCCAGTAT

AAATTAAAGC CCCATTCATC ATGGCACCAA TTGCTGCACA TGGTTTAGCC
   TTTAATTTCG GGGTAAGTAG TACCGTGGTT AACGACGTGT ACCAAATCGG

CACACTACTA AAGAAGCTGG TACTGCACGT GCAGTTTCAG AATTTGGTAC
   GTGTGATGAT TTCTTCGACC ATGACGTGCA CGTCAAAGTC TTAAACCATG

AATTATGTCC ATCTCAGCTT~ATTCTGGTGC AACATTTGAA GAAATTTCTG
   TTAATACAGG TAGAGTCGAA TAAGACCACG TTGTAAACTT CTTTAAAGAC

AAGGCTTAAA TGGCGGACCC CGTTGGTTCC AAATCTATAT GGCTAAAGAT
   TTCCGAATTT ACCGCCTGGG GCAACCAAGG TTTAGATATA CCGATTTCTA

GACCAACAAA ACCGTGATAT CTTAGACGGA GCTAAATCTG ATGGTGCAAC
   CTGGTTGTTT TGGCACTATA GAATCTGCCT CGATTTAGAC TACCACGTTG

TGCTATCATC CTTACAGCTG ACTCAACTGT TTCTGGAAAC CGTGACCGTG
   ACGATAGTAG GAATGTCGAC TGAGTTGACA AAGACCTTTG GCACTGGCAC

ATGTGAAGAA TAAATTCGTT TACCCATTTG GTATGCCAAT TGTTCAACGT
   TACACTTCTT ATTTAAGCAA ATGGGTAAAC CATACGGTTA ACAAGTTGCA

TACTTACGTG GTACAGCAGA AGGTATGTCA TTAAACAATA TCTACGGTGC
   ATGAATGCAC CATGTCGTCT TCCATACAGT AATTTGTTAT AGATGCCACG
```

FIG. 1

```
TTCAAAACAA AAAATCTCAC CAAGAGATAT TGAGGAAATC GCCGCTCATT
AAGTTTTGTT TTTTAGAGTG GTTCTCTATA ACTCCTTTAG CGGCGAGTAA

CTGGATTACC AGTATTCGTT AAAGGTATTC AACACCCAGA AGATGCAGAT
GACCTAATGG TCATAAGCAA TTTCCATAAG TTGTGGGTCT TCTACGTCTA

ATGGCAATCA AAGCTGGTGC ATCAGGTATC TGGGTATCTA ACCACGGTGC
TACCGTTAGT TTCGACCACG TAGTCCATAC ACCCATAGAT TGGTGCCACG

TCGTCAACTA TATGAAGCTC CAGGTTCAT1 TGACACCCT1 CCAGCTATTG
AGCAGTTGAT ATACTTCGAG GTCCAAGTAA ACTGTGGGAA GGTCGATAAC

CTGAACGTGT AAACAAACGT GTACCAATCG TCTTTGATTC AGGTGTACGT
GACTTGCACA TTTGTTTGCA CATGGTTAGC AGAAACTAAG TCCACATGCA

CGTGGTGAAC ACGTTGCCAA AGCGCTAGCT TCAGGGGCAG ACGTTGTTGC
GCACCACTTG TGCAACGGTT TCGCGATCGA AGTCCCCGTC TGCAACAACG

TTTAGGACGC CCAGTCTTAT TTGGTTTAGC TTTAGGTGGC TGGCAAGGTG
AAATCCTGCG GGTCAGAATA AACCAAATCG AAATCCACCG ACCGTTCCAC

CTTACTCAGT ACTTGACTAC TTCCAAAAAG ACTTAACACG CGTAATGCAA
GAATGAGTCA TGAACTGATG AAGGTTTTC TGAATTGTGC GCATTACGTT

TTAACAGGTT CACAAAATGT GGAAGACTTG AAGGGTCTAG ATTTATTCGA
AATTGTCCAA GTGTTTTACA CCTTCTGAAC TTCCCAGATC TAAATAAGCT

TAACCCATAC GGTTATGAAT AC 3'
ATTGGGTATG CCAATACTTA TG 5'
```

FIG. 2

```
5' ATGAATAACA ATGACATTGA ATATAATGCA CCTAGTGAAA TCAAGTACAT
3' TACTTATTGT TACTGTAACT TATATTACGT GGATCACTTT AGTTCATGTA

TGATGTTGTC AATACTTACG ACTTAGAAGA AGAAGCAAGT AAAGTGGTAC
   ACTACAACAG TTATGAATGC TGAATCTTCT TCTTCGTTCA TTTCACCATG

CACATGGTGG TTTTAACTAT ATTGCTGGTG CATCTGGTGA TGAGTGGACT
   GTGTACCACC AAAATTGATA TAACGACCAC GTAGACCACT ACTCACCTGA

AAACGCGCTA ATGACCGTGC TTGGAAACAT AAATTACTAT ACCCACGTCT
   TTTGCGCGAT TACTGGCACG AACCTTTGTA TTTAATGATA TGGGTGCAGA

AGCGCAAGAT GTTGAAGCGC CGATACAAG TACTGAAATT TTAGGTCATA
   TCGCGTTCTA CAACTTCGCG GCTATGTTC ATGACTTTAA AATCCAGTAT

AAATTAAAGC CCCATTCATC ATGGCACCAA TTGCTGCACA TGGTTTAGCC
   TTTAATTTCG GGGTAAGTAG TACCGTGGTT AACGACGTGT ACCAAATCGG

CACACTACTA AAGAAGCTGG TACTGCACGT GCAGTTTCAG AATTTGGTAC
   GTGTGATGAT TTCTTCGACC ATGACGTGCA CGTCAAAGTC TTAAACCATG

AATTATGTCC ATCTCAGCTT ATTCTGGTGC AACATTTGAA GAAATTTCTG
   TTAATACAGG TAGAGTCGAA TAAGACCACG TTGTAAACTT CTTTAAAGAC

AAGGCTTAAA TGGCGGACCC CGTTGGTTCC AAATCTATAT GGCTAAAGAT
   TTCCGAATTT ACCGCCTGGG GCAACCAAGG TTTAGATATA CCGATTTCTA

GACCAACAAA ACCGTGATAT CTTAGACGAA GCTAAATCTG ATGGTGCAAC
   CTGGTTGTTT TGGCACTATA GAATCTGCTT CGATTTAGAC TACCACGTTG

TGCTATCATC CTTACAGCTG ACTCAACTGT TTCTGGAAAC CGTGACCGTG
   ACGATAGTAG GAATGTCGAC TGAGTTGACA AAGACCTTTG GCACTGGCAC

ATGTGAAGAA TAAATTCGTT TACCCATTTG GTATGCCAAT TGTTCAACGT
   TACACTTCTT ATTTAAGCAA ATGGGTAAAC CATACGGTTA ACAAGTTGCA

TACTTACGTG GTACAGCAGA AGGTATGTCA TTAGACAATA TCTACGGTGC
   ATGAATGCAC CATGTCGTCT TCCATACAGT AATCTGTTAT AGATGCCACG
```

FIG. 3

```
TTCAAAACAA AAAATCTCAC CAAGAGATAT TGAGGAAATC GCCGCTCATT
AAGTTTTGTT TTTTAGAGTG GTTCTCTATA ACTCCTTTAG CGGCGAGTAA

CTGGATTACC AGTATTCGTT AAAGGTATTC AACACCCAGA AGATGCAGAT
GACCTAATGG TCATAAGCAA TTTCCATAAG TTGTGGGTCT TCTACGTCTA

ATGGCAATCA AAGCTGGTGC ATCAGGTATC TGGGTATCTA ACCACGGTGC
TACCGTTAGT TTCGACCACG TAGTCCATAG ACCCATAGAT TGGTGCCACG

TCGTCAACTA TATGAAGCTC CAGGTTCATT TGACACCCTT CCAGCTATTG
AGCAGTTGAT ATACTTCGAG GTCCAAGTAA ACTGTGGGAA GGTCGATAAC

CTGAACGTGT AAACAAACGT GTACCAATCG TCTTTGATTC AGGTGTACGT
GACTTGCACA TTTGTTTGCA CATGGTTAGC AGAAACTAAG TCCACATGCA

CGTGGTGAAC ACGTTGCCAA AGCGCTAGCT TCAGGGGCAG ACGTTGTTGC
GCACCACTTG TGCAACGGTT TCGCGATCGA AGTCCCCGTC TGCAACAACG

TTTAGGACGC CCAGTCTTAT TTGGTTTAGC TTTAGGTGGC TGGCAAGGTG
AAATCCTGCG GGTCAGAATA AACCAAATCG AAATCCACCG ACCGTTCCAC

CTTACTCAGT ACTTGACTAC TTCCAAAAAG ACTTAACACG CGTAATGCAA
GAATGAGTCA TGAACTGATG AAGGTTTTTC TGAATTGTGC GCATTACGTT

TTAACAGGTT CACAAAATGT GGAAGACTTG AAGGGTCTAG ATTTATTCGA
AATTGTCCAA GTGTTTTACA CCTTCTGAAC TTCCCAGATC TAAATAAGCT

TAACCCATAC GGTTATGAAT AC 3'
ATTGGGTATG CCAATACTTA TG 5'
```

FIG. 4

```
5' ATGAATAACA ATGACATTGA ATATAATGCA CCTAGTGAAA TCAAGTACAT
3' TACTTATTGT TACTGTAACT TATATTACGT GGATCACTTT AGTTCATGTA

TGATGTTGTC AATACTTACG ACTTAGAAGA AGAAGCAAGT AAAGTGGTAC
   ACTACAACAG TTATGAATGC TGAATCTTCT TCTTCGTTCA TTTCACCATG

CACATGGTGG TTTTAACTAT ATTGCTGGTG CATCTGGTGA TGAGTGGACT
   GTGTACCACC AAAATTGATA TAACGACCAC GTAGACCACT ACTCACCTGA

AAACGCGCTA ATGACCGTGC TTGGAAACAT AAATTACTAT ACCCACGTCT
   TTTGCGCGAT TACTGGCACG AACCTTTGTA TTTAATGATA TGGGTGCAGA

AGCGCAAGAT GTTGAAGCGC CCGATACAAG TACTGAAATT TTAGGTCATA
   TCGCGTTCTA CAACTTCGCG GGCTATGTTC ATGACTTTAA AATCCAGTAT

AAATTAAAGC CCCATTCATC ATGGCACCAA TTGCTGCACA TGGTTTAGCC
   TTTAATTTCG GGGTAAGTAG TACCGTGGTT AACGACGTGT ACCAAATCGG

CACACTACTA AAGAAGCTGG TACTGCACGT GCAGTTTCAG AATTTGGTAC
   GTGTGATGAT TTCTTCGACC ATGACGTGCA CGTCAAAGTC TTAAACCATG

AATTATGTCC ATCTCAGCTT ATTCTGGTGC AACATTTGAA GAAATTTCTG
   TTAATACAGG TAGAGTCGAA TAAGACCACG TTGTAAACTT CTTTAAAGAC

AAGGCTTAAA TGGCGGACCC CGTTGGTTCC AAATCTATAT GGCTAAAGAT
   TTCCGAATTT ACCGCCTGGG GCAACCAAGG TTTAGATATA CCGATTTCTA

GACCAACAAA ACCGTGATAT CTTAGACGGA GCTAAATCTG ATGGTGCAAC
   CTGGTTGTTT TGGCACTATA GAATCTGCCT CGATTTAGAC TACCACGTTG

TGCTATCATC CTTACAGCTG ACTCAACTGT TTCTGGAAAC CGTGACCGTG
   ACGATAGTAG GAATGTCGAC TGAGTTGACA AAGACCTTTG GCACTGGCAC

ATGTGAAGAA TAAATTCGTT TACCCATTTG GTATGCCAAT TGTTCAACGT
   TACACTTCTT ATTTAAGCAA ATGGGTAAAC CATACGGTTA ACAAGTTGCA

TACTTACGTG GTACAGCAGA AGGTATGTCA TTAGACAATA TCTACGGTGC
   ATGAATGCAC CATGTCGTCT TCCATACAGT AATCTGTTAT AGATGCCACG
```

FIG. 5

```
TTCAAAACAA AAAATCTCAC CAAGAGATAT TGAGGAAATC GCCGCTCATT
AAGTTTTGTT TTTTAGAGTG GTTCTCTATA ACTCCTTTAG CGGCGAGTAA

CTGGATTACC AGTATTCGTT AAAGGTATTC AACACCCAGA AGATGCAGAT
GACCTAATGG TCATAAGCAA TTTCCATAAG TTGTGGGTCT TCTACGTCTA

ATGGCAATCA AAGCTGGTGC ATCAGGTATC TGGGTATCTA ACCACGGTGC
TACCGTTAGT TTCGACCACG TAGTCCATAG ACCCATAGAT TGGTGCCACG

TCGTCAACTA TATGAAGCTC CAGGTTCATT TGACACCCTT CCAGCTATTG
AGCAGTTGAT ATACTTCGAG GTCCAAGTAA ACTGTGGGAA GGTCGATAAC

CTGAACGTGT AAACAAACGT GTACCAATCG TCTTTGATTC AGGTGTACGT
GACTTGCACA TTTGTTTGCA CATGGTTAGC AGAAACTAAG TCCACATGCA

CGTGGTGAAC ACGTTGCCAA AGCGCTAGCT TCAGGGGCAG ACGTTGTTGC
GCACCACTTG TGCAACGGTT TCGCGATCGA AGTCCCGTC TGCAACAACG

TTTAGGACGC CCAGTCTTAT TTGGTTTAGC TTTAGGTGGC TGGCAAGGTG
AAATCCTGCG GGTCAGAATA AACCAAATCG AAATCCACCG ACCGTTCCAC

CTTACTCAGT ACTTGACTAC TTCCAAAAAG ACTTAACACG CGTAATGCAA
GAATGAGTCA TGAACTGATG AAGGTTTTTC TGAATTGTGC GCATTACGTT

TTAACAGGTT CACAAAATGT GGAAGACTTG AAGGGTCTAG ATTTATTCGA
AATTGTCCAA GTGTTTTACA CCTTCTGAAC TTCCCAGATC TAAATAAGCT

TAACCCATAC GGTTATGAAT AC 3'
ATTGGGTATG CCAATACTTA TG 5'
```

FIG. 6

5'ATGAATAACAATGACATTGAATATAATGCACCTAGTGAAATCAAGTACATTGATGTTGTCAATACTTACGACTTAGAAGA3' ←(a)
3'TACTTATTGTTACTGTAACTTATATTACGTGGATCATTTAGTTCATGTAACAACAGTTATGAATGCTGAATCTTCTTCTTCGTT5' ←(b)

5'AGAAGCAAGTAAAGTGGTACCACATGGTGGTTTTAACTATATTGCTGGTGCATCTGGTGATGAGTGGACTAAACGCGCTAATGAC3' ←(c)
3'CATTTCACCATGGTGTACCACCAAAATTGATATAACGACCACTACTCACCTGATTTGCGC5' ←(d)

FIG. 7

LACTATE OXIDASE WITH AN IMPROVED THERMAL STABILITY AND GENE OF THE SAME

BACKGROUND OF THE INVENTION

The present invention relates to a lactate oxidase useful as an enzyme for a reaction which is represented by "L-lactate+oxygen→pyruvic acid+hydrogen peroxide". The lactate oxidase is an enzyme useful for a reaction to generate pyruvic acid and hydrogen peroxide from L-lactate and oxygen. Such lactate oxidase is extremely useful to measure a concentration of a lactic acid in a body fluid such as blood. It has been known in the art, to which the present invention pertains, that the lactate oxidase is present in bacteria which are classified into Pediococcus genus, Streptococcus genus, and Aerococcus genus. This is disclosed in the Japanese Laid-open Patent Applications Nos. 58-4557 and 2-177886 as well as in the Japanese Patent Publication No. 59-10190.

It was confirmed that a lactate oxidase obtained from Streptococcus shows a relatively low thermal stability. At a temperature above 34° C., the biological activity of this lactate oxidase is rapidly reduced. This is disclosed in the Japanese Patent Application No. 58-4557.

It was also confirmed that another lactate oxidase obtained from Aerococcus also shows a relatively low thermal stability. If this lactate oxidase is subjected to a heat treatment at a temperature of 65° C. for ten minutes, the biological activity is reduced by 50% or more. This is disclosed in the Japanese Patent Application No. 59-10190.

SUMMARY OF THE INVENTION

Accordingly, it is an object of the present invention to provide a lactate oxidase showing a sufficiently high thermal stability.

It is a further object of the present invention to provide a gene which codes on expression for a lactate oxidase showing a sufficiently high thermal stability.

The above and other objects, features and advantages of the present invention will be apparent from the following descriptions.

The present invention provides a lactate oxidase (LOD15) which shows an enzymatic activity under a reaction represented by "L-lactate+oxygen→pyruvic acid+hydrogen peroxide" and which has amino acid sequences (SEQ ID NO:2):

| Met | Asn | Asn | Asn | Asp | Ile | Glu | Tyr | Asn | Ala | 10 |
|---|---|---|---|---|---|---|---|---|---|---|
| Pro | Ser | Glu | Ile | Lys | Tyr | Ile | Asp | Val | Val | 20 |
| Asn | Thr | Tyr | Asp | Leu | Glu | Glu | Glu | Ala | Ser | 30 |
| Lys | Val | Val | Pro | His | Gly | Gly | Phe | Asn | Tyr | 40 |
| Ile | Ala | Gly | Ala | Ser | Gly | Asp | Glu | Trp | Thr | 50 |
| Lys | Arg | Ala | Asn | Asp | Arg | Ala | Trp | Lys | His | 60 |
| Lys | Leu | Leu | Tyr | Pro | Arg | Leu | Ala | Gln | Asp | 70 |
| Val | Glu | Ala | Pro | Asp | Thr | Ser | Thr | Glu | Ile | 80 |
| Leu | Gly | His | Lys | Ile | Lys | Ala | Pro | Phe | Ile | 90 |
| Met | Ala | Pro | Ile | Ala | Ala | His | Gly | Leu | Ala | 100 |
| His | Thr | Thr | Lys | Glu | Ala | Gly | Thr | Ala | Arg | 110 |
| Ala | Val | Ser | Glu | Phe | Gly | Thr | Ile | Met | Ser | 120 |
| Ile | Ser | Ala | Tyr | Ser | Gly | Ala | Thr | Phe | Glu | 130 |
| Glu | Ile | Ser | Glu | Gly | Leu | Asn | Gly | Gly | Pro | 140 |
| Arg | Trp | Phe | Gln | Ile | Tyr | Met | Ala | Lys | Asp | 150 |
| Asp | Gln | Gln | Asn | Arg | Asp | Ile | Leu | Asp | Glu | 160 |
| Ala | Lys | Ser | Asp | Gly | Ala | Thr | Ala | Ile | Ile | 170 |
| Leu | Thr | Ala | Asp | Ser | Thr | Val | Ser | Gly | Asn | 180 |
| Arg | Asp | Arg | Asp | Val | Lys | Asn | Lys | Phe | Val | 190 |
| Tyr | Pro | Phe | Gly | Met | Pro | Ile | Val | Gln | Arg | 200 |
| Tyr | Leu | Arg | Gly | Thr | Ala | Glu | Gly | Met | Ser | 210 |
| Leu | Asp | Asn | Ile | Tyr | Gly | Ala | Ser | Lys | Gln | 220 |
| Lys | Ile | Ser | Pro | Arg | Asp | Ile | Glu | Glu | Ile | 230 |
| Ala | Ala | His | Ser | Gly | Leu | Pro | Val | Phe | Val | 240 |
| Lys | Gly | Ile | Gln | His | Pro | Glu | Asp | Ala | Asp | 250 |
| Met | Ala | Ile | Lys | Ala | Gly | Ala | Ser | Gly | Ile | 260 |
| Trp | Val | Ser | Asn | His | Gly | Ala | Arg | Gln | Leu | 270 |
| Tyr | Glu | Ala | Pro | Gly | Ser | Phe | Asp | Thr | Leu | 280 |
| Pro | Ala | Ile | Ala | Glu | Arg | Val | Asn | Lys | Arg | 290 |
| Val | Pro | Ile | Val | Phe | Asp | Ser | Gly | Val | Arg | 300 |
| Arg | Gly | Glu | His | Val | Ala | Lys | Ala | Leu | Ala | 310 |
| Ser | Gly | Ala | Asp | Val | Val | Ala | Leu | Gly | Gly | 320 |
| Pro | Val | Leu | Phe | Gly | Leu | Ala | Leu | Gly | Gly | 330 |
| Trp | Gln | Gly | Ala | Tyr | Ser | Val | Leu | Asp | Tyr | 340 |
| Phe | Gln | Lys | Asp | Leu | Thr | Arg | Val | Met | Gln | 350 |
| Leu | Thr | Gly | Ser | Gln | Asn | Val | Glu | Asp | Leu | 360 |
| Lys | Gly | Leu | Asp | Leu | Phe | Asp | Asn | Pro | Tyr | 370 |
| Gly | Tyr | Glu | Tyr | 374 | | | | | | |

The above amino acid sequences of the lactate oxidase (LOD15) differ from those of the latate oxidase obtained from Aerococcus in an amino acid only which is underlined and positioned at 212th position. In the above amino acid sequences of the lactate oxidase (LOD15), the amino acid positioned at 212th position is "Asp" or aspartic acid. By contrast, in the amino acid sequences of the lactate oxidase obtained from Aerococcus, the amino acid positioned at 212th position is "Asn" or asparagine.

The present invention provides a DNA molecule comprising nucleotide sequences which code on expression for a lactate oxidase (LOD15) showing an enzymatic activity under a reaction represented by "L-lactate+oxygen→pyruvic acid+hydrogen peroxide", wherein the nucleotide sequences (SEQ ID NO:2) are:

| | | | | | | | | | | |
|---|---|---|---|---|---|---|---|---|---|---|
| ATG | AAT | AAC | AAT | GAC | ATT | GAA | TAT | AAT | GCA | 30 |
| CCT | AGT | GAA | ATC | AAG | TAC | ATT | GAT | GTT | GTC | 60 |
| AAT | ACT | TAC | GAC | TTA | GAA | GAA | GAA | GCA | AGT | 90 |
| AAA | GTG | GTA | CCA | CAT | GGT | GGT | TTT | AAC | TAT | 120 |
| ATT | GCT | GGT | GCA | TCT | GGT | GAT | GAG | TGG | ACT | 150 |
| AAA | CGC | GCT | AAT | GAC | CGT | GCT | TGG | AAA | CAT | 180 |
| AAA | TTA | CTA | TAC | CCA | CGT | CTA | GCG | CAA | GAT | 210 |
| GTT | GAA | GCG | CCC | GAT | ACA | AGT | ACT | GAA | ATT | 240 |
| TTA | GGT | CAT | AAA | ATT | AAA | GCC | CCA | TTC | ATC | 270 |
| ATG | GCA | CCA | ATT | GCT | GCA | CAT | GGT | TTA | GCC | 300 |
| CAC | ACT | ACT | AAA | GAA | GCT | GGT | ACT | GCA | CGT | 330 |
| GCA | GTT | TCA | GAA | TTT | GGT | ACA | ATT | ATG | TCC | 360 |
| ATC | TCA | GCT | TAT | TCT | GGT | GCA | ACA | TTT | GAA | 390 |
| GAA | ATT | TCT | GAA | GGC | TTA | AAT | GGC | GGA | CCC | 420 |
| CGT | TGG | TTC | CAA | ATC | TAT | ATG | GCT | AAA | GAT | 450 |
| GAC | CAA | CAA | AAC | CGT | GAT | ATC | TTA | GAC | GAA | 480 |
| GCT | AAA | TCT | GAT | GGT | GCA | ACT | GCT | ATC | ATC | 510 |
| CTT | ACA | GCT | GAC | TCA | ACT | GTT | TCT | GGA | AAC | 540 |
| CGT | GAC | CGT | GAT | GTG | AAG | AAT | AAA | TTC | GTT | 570 |
| TAC | CCA | TTT | GGT | ATG | CCA | ATT | GTT | CAA | CGT | 600 |
| TAC | TTA | CGT | GGT | ACA | GCA | GAA | GGT | ATG | TCA | 630 |
| TTA | GAC | AAT | ATC | TAC | GGT | GCT | TCA | AAA | CAA | 660 |
| AAA | ATC | TCA | CCA | AGA | GAT | ATT | GAG | GAA | ATC | 690 |
| GCC | GCT | CAT | TCT | GGA | TTA | CCA | GTA | TTC | GTT | 720 |
| AAA | GGT | ATT | CAA | CAC | CCA | GAA | GAT | GCA | GAT | 750 |
| ATG | GCA | ATC | AAA | GCT | GGT | GCA | TCA | GGT | ATC | 780 |
| TGG | GTA | TCT | AAC | CAC | GGT | GCT | CGT | CAA | CTA | 810 |
| TAT | GAA | GCT | CCA | GGT | TCA | TTT | GAC | ACC | CTT | 840 |
| CCA | GCT | ATT | GCT | GAA | CGT | GTA | AAC | AAA | CGT | 870 |
| GTA | CCA | ATC | GTC | TTT | GAT | TCA | GGT | GTA | CGT | 900 |
| CGT | GGT | GAA | CAC | GTT | GCC | AAA | GCG | CTA | GCT | 930 |
| TCA | GGG | GCA | GAC | GTT | GTT | GCT | TTA | GGA | CGC | 960 |
| CCA | GTC | TTA | TTT | GGT | TTA | GCT | TTA | GGT | GGC | 990 |
| TGG | CAA | GGT | GCT | TAC | TCA | GTA | CTT | GAC | TAC | 1020 |
| TTC | CAA | AAA | GAC | TTA | ACA | CGC | GTA | ATG | CAA | 1050 |
| TTA | ACA | GGT | TCA | CAA | AAT | GTG | GAA | GAC | TTG | 1080 |
| AAG | GGT | CTA | GAT | TTA | TTC | GAT | AAC | CCA | TAC | 1110 |
| GGT | TAT | GAA | TAC | 1122 | | | | | | |

The nucleotide sequences of the lactate oxidase (LOD15) differ from those the latate oxidase obtained from Aerococcus in a nucleotide only which is underlined and positioned at 634th position. In the above nucleotide sequences for the lactate oxidase (LOD15), the nucleotide positioned at 634th position is "G" or guanine. By contrast, in the nucleotide sequences for the lactate oxidase obtained from Aerococcus, the nucleotide positioned at 634th position is "A" or adenine.

The present invention provides a lactate oxidase (LOD1) which shows an enzymatic activity under a reaction represented by "L-lactate+oxygen→pyruvic acid+hydrogen peroxide" and which has amino acid sequences (SEQ ID NO:4):

| | | | | | | | | | | |
|---|---|---|---|---|---|---|---|---|---|---|
| Met | Asn | Asn | Asn | Asp | Ile | Glu | Tyr | Asn | Ala | 10 |
| Pro | Ser | Glu | Ile | Lys | Tyr | Ile | Asp | Val | Val | 20 |
| Asn | Thr | Tyr | Asp | Leu | Glu | Glu | Glu | Ala | Ser | 30 |
| Lys | Val | Val | Pro | His | Gly | Gly | Phe | Asn | Tyr | 40 |
| Ile | Ala | Gly | Ala | Ser | Gly | Asp | Glu | Trp | Thr | 50 |
| Lys | Arg | Ala | Asn | Asp | Arg | Ala | Trp | Lys | His | 60 |
| Lys | Leu | Leu | Tyr | Pro | Arg | Leu | Ala | Gln | Asp | 70 |
| Val | Glu | Ala | Pro | Asp | Thr | Ser | Thr | Glu | Ile | 80 |
| Leu | Gly | His | Lys | Ile | Lys | Ala | Pro | Phe | Ile | 90 |
| Met | Ala | Pro | Ile | Ala | Ala | His | Gly | Leu | Ala | 100 |
| His | Thr | Thr | Lys | Glu | Ala | Gly | Thr | Ala | Arg | 110 |
| Ala | Val | Ser | Glu | Phe | Gly | Thr | Ile | Met | Ser | 120 |
| Ile | Ser | Ala | Tyr | Ser | Gly | Ala | Thr | Phe | Glu | 130 |
| Glu | Ile | Ser | Glu | Gly | Leu | Asn | Gly | Gly | Pro | 140 |
| Arg | Trp | Phe | Gln | Ile | Tyr | Met | Ala | Lys | Asp | 150 |
| Asp | Gln | Gln | Asn | Arg | Asp | Ile | Leu | Asp | Gly | 160 |
| Ala | Lys | Ser | Asp | Gly | Ala | Thr | Ala | Ile | Ile | 170 |
| Leu | Thr | Ala | Asp | Ser | Thr | Val | Ser | Gly | Asn | 180 |
| Arg | Asp | Arg | Asp | Val | Lys | Asn | Lys | Phe | Val | 190 |
| Tyr | Pro | Phe | Gly | Met | Pro | Ile | Val | Gln | Arg | 200 |
| Tyr | Leu | Arg | Gly | Thr | Ala | Glu | Gly | Met | Ser | 210 |
| Leu | Asn | Asn | Ile | Tyr | Gly | Ala | Ser | Lys | Gln | 220 |
| Lys | Ile | Ser | Pro | Arg | Asp | Ile | Glu | Glu | Ile | 230 |

-continued

| Ala | Ala | His | Ser | Gly | Leu | Pro | Val | Phe | Val | 240 |
| Lys | Gly | Ile | Gln | His | Pro | Glu | Asp | Ala | Asp | 250 |
| Met | Ala | Ile | Lys | Ala | Gly | Ala | Ser | Gly | Ile | 260 |
| Trp | Val | Ser | Asn | His | Gly | Ala | Arg | Gln | Leu | 270 |
| Tyr | Glu | Ala | Pro | Gly | Ser | Phe | Asp | Thr | Leu | 280 |
| Pro | Ala | Ile | Ala | Glu | Arg | Val | Asn | Lys | Arg | 290 |
| Val | Pro | Ile | Val | Phe | Asp | Ser | Gly | Val | Arg | 300 |
| Arg | Gly | Glu | His | Val | Ala | Lys | Ala | Leu | Ala | 310 |
| Ser | Gly | Ala | Asp | Val | Val | Ala | Leu | Gly | Arg | 320 |
| Pro | Val | Leu | Phe | Gly | Leu | Ala | Leu | Gly | Gly | 330 |
| Trp | Gln | Gly | Ala | Tyr | Ser | Val | Leu | Asp | Tyr | 340 |
| Phe | Gln | Lys | Asp | Leu | Thr | Arg | Val | Met | Gln | 350 |
| Leu | Thr | Gly | Ser | Gln | Asn | Val | Glu | Asp | Leu | 360 |
| Lys | Gly | Leu | Asp | Leu | Phe | Asp | Asn | Pro | Tyr | 370 |
| Gly | Tyr | Glu | Tyr | 374 | | | | | | |

The above amino acid sequences of the lactate oxidase (LOD1) differ from those of the latate oxidase obtained from Aerococcus in an amino acid only which is underlined and positioned at 160th position. In the above amino acid sequences of the lactate oxidase (LOD1), the amino acid positioned at 160th position is "Gly" or glycine. By contrast, in the amino acid sequences of the lactate oxidase obtained from Aerococcus, the amino acid positioned at 160th position is "Glu" or Glutamic acid.

The present invention provides a DNA molecule comprising nucleotide sequences which code on expression for a lactate oxidase (LOD1) showing an enzymatic activity under a reaction represented by "L-lactate+oxygen→pyruvic acid+hydrogen peroxide", wherein the nucleotide sequences (SEQ ID NO:3) are:

The nucleotide sequences of the lactate oxidase (LOD1) differ from those the latate oxidase obtained from Aerococcus in a nucleotide only which is underlined and positioned at 479th position. In the above nucleotide sequences for the lactate oxidase (LOD1), the nucleotide positioned at 479th position is "G" or guanine. By contrast, in the nucleotide sequences for the lactate oxidase obtained from Aerococcus, the nucleotide positioned at 479th position is "A" or adenine.

The present invention provides a lactate oxidase (LOD16) which shows an enzymatic activity under a reaction represented by "L-lactate+oxygen→pyruvic acid+hydrogen peroxide" and which has amino acid sequences (SEQ ID NO:6):

| ATG | AAT | AAC | AAT | GAC | ATT | GAA | TAT | AAT | GCA | 30 |
| CCT | AGT | GAA | ATC | AAG | TAC | ATT | GAT | GTT | GTC | 60 |
| AAT | ACT | TAC | GAC | TTA | GAA | GAA | GAA | GCA | AGT | 90 |
| AAA | GTG | GTA | CCA | CAT | GGT | GGT | TTT | AAC | TAT | 120 |
| ATT | GCT | GGT | GCA | TCT | GGT | GAT | GAG | TGG | ACT | 150 |
| AAA | CGC | GCT | AAT | GAC | CGT | GCT | TGG | AAA | CAT | 180 |
| AAA | TTA | CTA | TAC | CCA | CGT | CTA | GCG | CAA | GAT | 210 |
| GTT | GAA | GCG | CCC | GAT | ACA | AGT | ACT | GAA | ATT | 240 |
| TTA | GCT | CAT | AAA | ATT | AAA | GCC | CCA | TTC | ATC | 270 |
| ATG | GCA | CCA | ATT | GCT | GCA | CAT | GGT | TTA | GCC | 300 |
| CAC | ACT | ACT | AAA | GAA | GCT | GGT | ACT | GCA | CGT | 330 |
| GCA | GTT | TCA | GAA | TTT | GGT | ACA | ATT | ATG | TCC | 360 |
| ATC | TCA | GCT | TAT | TCT | GGT | GCA | ACA | TTT | GAA | 390 |
| GAA | ATT | TCT | GAA | GGC | TTA | AAT | GGC | GGA | CCC | 420 |
| CGT | TGG | TTC | CAA | ATC | TAT | ATG | GCT | AAA | GAT | 450 |
| GAC | CAA | CAA | AAC | CGT | GAT | ATC | TTA | GAC | GGA | 480 |
| GCT | AAA | TCT | GAT | GGT | GCA | ACT | GCT | ATC | ATC | 510 |
| CTT | ACA | GCT | GAC | TCA | ACT | GTT | TCT | GGA | AAC | 540 |
| CGT | GAC | CGT | GAT | GTG | AAG | AAT | AAA | TTC | GTT | 570 |
| TAC | CCA | TTT | GGT | ATG | CCA | ATT | GTT | CAA | CGT | 600 |
| TAC | TTA | CGT | GGT | ACA | GCA | GAA | GGT | ATG | TCA | 630 |
| TTA | AAC | AAT | ATC | TAC | GGT | GCT | TCA | AAA | CAA | 660 |
| AAA | ATC | TCA | CCA | AGA | GAT | ATT | GAG | GAA | ATC | 690 |
| GCC | GCT | CAT | TCT | GGA | TTA | CCA | GTA | TTC | GTT | 720 |
| AAA | GGT | ATT | CAA | CAC | CCA | GAA | GAT | GCA | GAT | 750 |
| ATG | GCA | ATC | AAA | GCT | GGT | GCA | TCA | GGT | ATC | 780 |
| TGG | GTA | TCT | AAC | CAC | GGT | GCT | CGT | CAA | CTA | 810 |
| TAT | GAA | GCT | CCA | GGT | TCA | TTT | GAC | ACC | CTT | 840 |
| CCA | GCT | ATT | GCT | GAA | CGT | GTA | AAC | AAA | CGT | 870 |
| GTA | CCA | ATC | GTC | TTT | GAT | TCA | GGT | GTA | CGT | 900 |
| CGT | GGT | GAA | CAC | GTT | GCC | AAA | GCG | CTA | GCT | 930 |
| TCA | GGG | GCA | GAC | GTT | GTT | GCT | TTA | GGA | CGC | 960 |
| CCA | GTC | TTA | TTT | GGT | TTA | GCT | TTA | GGT | GGC | 990 |
| TGG | CAA | GGT | GCT | TAC | TCA | GTA | CTT | GAC | TAC | 1020 |
| TTC | CAA | AAA | GAC | TTA | ACA | CGC | GTA | ATG | CAA | 1050 |
| TTA | ACA | GGT | TCA | CAA | AAT | GTG | GAA | GAC | TTG | 1080 |
| AAG | GGT | CTA | GAT | TTA | TTC | GAT | AAC | CCA | TAC | 1110 |
| GGT | TAT | GAA | TAC | 1122 | | | | | | |

| | | | | | | | | | |
|---|---|---|---|---|---|---|---|---|---|
| Met | Asn | Asn | Asn | Asp | Ile | Glu | Tyr | Asn | Ala | 10 |
| Pro | Ser | Glu | Ile | Lys | Tyr | Ile | Asp | Val | Val | 20 |
| Asn | Thr | Tyr | Asp | Leu | Glu | Glu | Glu | Ala | Ser | 30 |
| Lys | Val | Val | Pro | His | Gly | Gly | Phe | Asn | Tyr | 40 |
| Ile | Ala | Gly | Ala | Ser | Gly | Asp | Glu | Trp | Thr | 50 |
| Lys | Arg | Ala | Asn | Asp | Arg | Ala | Trp | Lys | His | 60 |
| Lys | Leu | Leu | Tyr | Pro | Arg | Leu | Ala | Gln | Asp | 70 |
| Val | Glu | Ala | Pro | Asp | Thr | Ser | Thr | Glu | Ile | 80 |
| Leu | Gly | His | Lys | Ile | Lys | Ala | Pro | Phe | Ile | 90 |
| Met | Ala | Pro | Ile | Ala | Ala | His | Gly | Leu | Ala | 100 |
| His | Thr | Thr | Lys | Glu | Ala | Gly | Thr | Ala | Arg | 110 |
| Ala | Val | Ser | Glu | Phe | Gly | Thr | Ile | Met | Ser | 120 |
| Ile | Ser | Ala | Tyr | Ser | Gly | Ala | Thr | Phe | Glu | 130 |
| Glu | Ile | Ser | Glu | Gly | Leu | Asn | Gly | Gly | Pro | 140 |
| Arg | Trp | Phe | Gln | Ile | Tyr | Met | Ala | Lys | Asp | 150 |
| Asp | Gln | Gln | Asn | Arg | Asp | Ile | Leu | Asp | Gly | 160 |
| Ala | Lys | Ser | Asp | Gly | Ala | Thr | Ala | Ile | Ile | 170 |
| Leu | Thr | Ala | Asp | Ser | Thr | Val | Ser | Gly | Asn | 180 |
| Arg | Asp | Arg | Asp | Val | Lys | Asn | Lys | Phe | Val | 190 |
| Tyr | Pro | Phe | Gly | Met | Pro | Ile | Val | Gln | Arg | 200 |
| Tyr | Leu | Arg | Gly | Thr | Ala | Glu | Gly | Met | Ser | 210 |
| Leu | Asp | Asn | Ile | Tyr | Gly | Ala | Ser | Lys | Gln | 220 |
| Lys | Ile | Ser | Pro | Arg | Asp | Ile | Glu | Glu | Ile | 230 |
| Ala | Ala | His | Ser | Gly | Leu | Pro | Val | Phe | Val | 240 |
| Lys | Gly | Ile | Gln | His | Pro | Glu | Asp | Ala | Asp | 250 |
| Met | Ala | Ile | Lys | Ala | Gly | Ala | Ser | Gly | Ile | 260 |
| Trp | Val | Ser | Asn | His | Gly | Ala | Arg | Gln | Leu | 270 |
| Tyr | Glu | Ala | Pro | Gly | Ser | Phe | Asp | Thr | Leu | 280 |
| Pro | Ala | Ile | Ala | Glu | Arg | Val | Asn | Lys | Arg | 290 |
| Val | Pro | Ile | Val | Phe | Asp | Ser | Gly | Val | Arg | 300 |
| Arg | Gly | Glu | His | Val | Ala | Lys | Ala | Leu | Ala | 310 |
| Ser | Gly | Ala | Asp | Val | Val | Ala | Leu | Gly | Arg | 320 |
| Pro | Val | Leu | Phe | Gly | Leu | Ala | Leu | Gly | Gly | 330 |
| Trp | Gln | Gly | Ala | Tyr | Ser | Val | Leu | Asp | Tyr | 340 |
| Phe | GLn | Lys | Asp | Leu | Thr | Arg | Val | Met | Gln | 350 |
| Leu | Thr | Gly | Ser | Gln | Asn | Val | Glu | Asp | Leu | 360 |
| Lys | Gly | Leu | Asp | Leu | Phe | Asp | Asn | Pro | Tyr | 370 |
| Gly | Tyr | Glu | Tyr | 374 | | | | | | |

The above amino acid sequences of the lactate oxidase (LOD16) differ from those of the latate oxidase obtained from Aerococcus in two amino acids only which are underlined and positioned at 160th and 212th positions. In the above amino acid sequences of the lactate oxidase (LOD16), the amino acid positioned at 160th position is "Gly" or glycine. By contrast, in the amino acid sequences of the lactate oxidase obtained from Aerococcus, the amino acid positioned at 160th position is "Glu" or Glutamic acid. Further, in the above amino acid sequences of the lactate oxidase (LOD16), the amino acid positioned at 212th position is "Asp" or aspartic acid. By contrast, in the amino acid sequences of the lactate oxidase obtained from Aerococcus, the amino acid positioned at 160th position is "Asn" or asparagin.

The present invention provides a DNA molecule comprising nucleotide sequences which code on expression for a lactate oxidase (LOD16) showing an enzymatic activity under a reaction represented by "L-lactate+ oxygen→pyruvic acid+hydrogen peroxide", wherein the nucleotide sequences (SEQ ID NO:5) are:

| | | | | | | | | | |
|---|---|---|---|---|---|---|---|---|---|
| ATG | AAT | AAC | AAT | GAC | ATT | GAA | TAT | AAT | GCA | 30 |
| CCT | AGT | GAA | ATC | AAG | TAC | ATT | GAT | GTT | GTC | 60 |
| AAT | ACT | TAC | GAC | TTA | GAA | GAA | GAA | GCA | AGT | 90 |
| AAA | GTG | GTA | CCA | CAT | GGT | GGT | TTT | AAC | TAT | 120 |
| ATT | GCT | GGT | GCA | TCT | GGT | GAT | GAG | TGG | ACT | 150 |
| AAA | CGC | GCT | AAT | GAC | CGT | GCT | TGG | AAA | CAT | 180 |
| AAA | TTA | CTA | TAC | CCA | CGT | CTA | GCG | CAA | GAT | 210 |
| GTT | GAA | GCG | CCC | GAT | ACA | AGT | ACT | GAA | ATT | 240 |
| TTA | GGT | CAT | AAA | ATT | AAA | GCC | CCA | TTC | ATC | 270 |
| ATG | GCA | CCA | ATT | GCT | GCA | CAT | GGT | TTA | GCC | 300 |
| CAC | ACT | ACT | AAA | GAA | GCT | GGT | ACT | GCA | CGT | 330 |
| GCA | GTT | TCA | GAA | TTT | GGT | ACA | ATT | ATG | TCC | 360 |
| ATC | TCA | GCT | TAT | TCT | GGT | GCA | ACA | TTT | GAA | 390 |
| GAA | ATT | TCT | GAA | GGC | TTA | AAT | GGC | GGA | CCC | 420 |
| CGT | TGG | TTC | CAA | ATC | TAT | ATG | GCT | AAA | GAT | 450 |
| GAC | CAA | CAA | AAC | CGT | GAT | ATC | TTA | GAC | GGA | 480 |
| GCT | AAA | TCT | GAT | GGT | GCA | ACT | GCT | ATC | ATC | 510 |
| CTT | ACA | GCT | GAC | TCA | ACT | GTT | TCT | GGA | AAC | 540 |
| CGT | GAC | CGT | GAT | GTG | AAG | AAT | AAA | TTC | GTT | 570 |
| TAC | CCA | TTT | GGT | ATG | CCA | ATT | GTT | CAA | CGT | 600 |
| TAC | TTA | CGT | GGT | ACA | GCA | GAA | GGT | ATG | TCA | 630 |

-continued

| | | | | | | | | | |
|---|---|---|---|---|---|---|---|---|---|
| TTA | GAC | AAT | ATC | TAC | GGT | GCT | TCA | AAA | CAA | 660 |
| AAA | ATC | TCA | CCA | AGA | GAT | ATT | GAG | GAA | ATC | 690 |
| GCC | GCT | CAT | TCT | GGA | TTA | CCA | GTA | TTC | GTT | 720 |
| AAA | GGT | ATT | CAA | CAC | CCA | GAA | GAT | GCA | GAT | 750 |
| ATG | GCA | ATC | AAA | GCT | GGT | GCA | TCA | GGT | ATC | 780 |
| TGG | GTA | TCT | AAC | CAC | GGT | GCT | CGT | CAA | CTA | 810 |
| TAT | GAA | GCT | CCA | GGT | TCA | TTT | GAC | ACC | CTT | 840 |
| CCA | GCT | ATT | GCT | GAA | CGT | GTA | AAC | AAA | CGT | 870 |
| GTA | CCA | ATC | GTC | TTT | GAT | TCA | GGT | GTA | CGT | 900 |
| CGT | GGT | GAA | CAC | GTT | GCC | AAA | GCG | CTA | GCT | 930 |
| TCA | GGG | GCA | GAC | GTT | GTT | GCT | TTA | GGA | CGC | 960 |
| CCA | GTC | TTA | TTT | GGT | TTA | GCT | TTA | GGT | GGC | 990 |
| TGG | CAA | GGT | GCT | TAC | TCA | GTA | CTT | GAC | TAC | 1020 |
| TTC | CAA | AAA | GAC | TTA | ACA | CGC | GTA | ATG | CAA | 1050 |
| TTA | ACA | GGT | TCA | CAA | AAT | GTG | GAA | GAC | TTG | 1080 |
| AAG | GGT | CTA | GAT | TTA | TTC | GAT | AAC | CCA | TAC | 1110 |
| GGT | TAT | GAA | TAC | 1122 | | | | | | |

The nucleotide sequences of the lactate oxidase (LOD16) differ from those the latate oxidase obtained from Aerococcus in two nucleotides only which are underlined and positioned at 479th and 634 positions. In the above nucleotide sequences for the lactate oxidase (LOD16), the nucleotide positioned at 479th position is "G" or guanine. By contrast, in the nucleotide sequences for the lactate oxidase obtained from Aerococcus, the nucleotide positioned at 479th position is "A" or adenine. In the above nucleotide sequences for the lactate oxidase (LOD16), the nucleotide positioned at 634th position is "G" or guanine, By contrast, in the nucleotide sequences for the lactate oxidase obtained from Aerococcus, the nucleotide positioned at 634th position is "A" or adenine.

BRIEF DESCRIPTIONS OF THE DRAWINGS

Preferred examples of the resent invention will be described in detail with reference to the accompanying drawings.

FIGS. 1 and 2 are views illustrative of nucleotide sequences of oligonucleotide "A" chemically synthesized.

FIGS. 3 and 4 are views illustrative of nucleotide sequences of oligonucleotide "B" chemically synthesized.

FIGS. 5 and 6 are views illustrative of nucleotide sequences of oligonucleotide "C" chemically synthesized.

FIG. 7 is a view illustrative of processes for chemical synthesis of DNAs.

DESCRIPTIONS OF THE INVENTION

Figure 8:
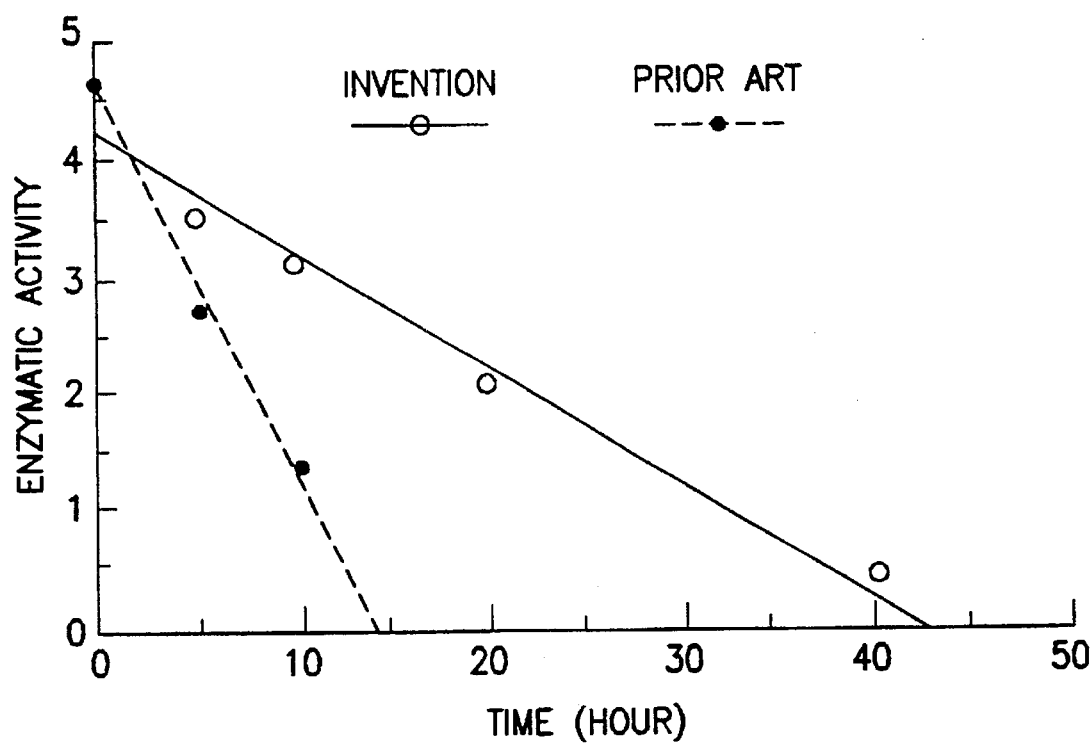
FIG. 8 is a diagram illustrative of variations in thermal stabilities over times of a novel lactate oxidase (LOD15) of the present invention and the conventional lactate obtained from Aerococcus.

The above lactate oxidases (LOD15, LOD1, LOD16) were obtained as follows. Polynucleotide fragment "A" illustrated in FIGS. 1 and 2, polynucleotide fragment "B" illustrated in FIGS. 3 and 4 and polynucleotide fragment "C" illustrated in FIGS. 5 and 6 were inserted into a vector for its expression in a host such as E. coli, and subsequent purifying process whereby lactate oxidases (LOD15, LOD1, LOD16) were obtained. The purified enzymes were then subjected to a heat treatment at a temperature of 65° C. for ten minutes. It was confirmed that the activity of the lactate oxidase (LOD15) after heat treatment is 20% of those before the heat treatment. It was also confirmed that the activity of the lactate oxidase (LOD1) after heat treatment is 56% of those before the heat treatment. It was also confirmed that the activity of the lactate oxidase (LOD16) after heat treatment is 43% of those before the heat treatment.

SYNTHESIS OF GENE FOR LACTATE OXIDASE

Synthesis of gene or lactate oxidase was carried out using DNA synthesizer "MODEL 380 DNA SYNTHESIZER" commercially available from Applied Biosystem Co., Ltd. in the known method disclosed in Science vol. 198, pp. 1056–1063, 1977. Single strands (a), (b), (c), and (d) in FIG. 7 of oligonucleotide were respectively synthesized. The synthesized oligonucleotides were treated with ammonia water either at a room temperature for 8 hours or at a temperature of 55° C. for 1 hour. The used ammonia water was then removed by rotary evaporator to carry out deblocking of the oligonucleotides. The deblocked oligonucleotides were purified using a reverse phase high performance liquid chromatography LC-10A commercially available from Shimazu Manufacturing Co. The purified oligonucleotides were subjected to 5'-end phosphorylation using T4 Polynucleotide Kinase commercially available from Takara.

The single strand oligonucleotides (a), (b), (c), and (d) were individually annealed. As a result, a double strand DNA fragment (ab) was obtained wherein 5'-end of one of the strands protrudes or is in the form of the single strand. Another double strand DNA fragment (cd) was obtained wherein 5'-end and 3'-end protrude or are in the form of the single strand. 5'-ends of the double strand DNA fragments (ab) and (cd) are ligasible or complement to each other. The double strand DNA fragments (ab) and (cd) were legated with each other via the 5'-ends thereof.

The above processes were repeated until any of the double strand oligonucleotides "A", "B" and "C" illustrated in FIGS. 1–2, FIGS. 3–4, and FIGS. 5–6. The obtained oligonucleotide was purified using an agarose gel electrophoresis which is disclosed in Molecular Cloning, Vol. 1, pp. 6.3–6.60 1989 and commercially available from Cold Spring Harbor Laboratory.

PREPARATION OF EXPRESSION VECTOR OF LACTATE OXIDASE

The above purified oligonucleotide "A", "B" or "C" were then inserted into an expression vector to prepare a lactate oxidase expression vector. For example, pKK223-3, commercially available from Pharmacia and disclosed in Proc. natl. Acad. Sci. USA, vol. 81, p. 6929, 1984, was cut with a restriction enzyme E. coli commercially available from Takara so that the cut end comes into blunt end for subsequent dephosphorization with Alkaline Phosphatase commercially available from Takara.

The above purified oligonucleotide "A", "B" or "C" were then inserted into the expression vector pKK223-3 using Sure Clone Ligation kit commercially available from Pharmacia Co. for elution of phenol and subsequent ethanol precipitation to thereby purify the same. This process is disclosed in Labomanual of Gene Engineering, pp. 29–33.

A plasmid obtained from the oligonucleotide "A" was named as pLOD15. A plasmid obtained from the oligonucleotide "B" was named as pLOD1. A plasmid obtained from the oligonucleotide "C" was named as pLOD16. Nucleotide sequences of pLOD15, pLOD1 and pLOD16 were analyzed using a DNA sequencer SQ-3000 of Hitachi in a dideoxy nucleotide sequencing method disclosed in Proc. Natl. Acad. Sci. USA, vol. 74, pp. 5463–5467, 1977.

EXPRESSION OF LATATE OXIDASE

The plasmid pLOD15, pLOD1or pLOD16 was inserted into a host cell. For example, the plasmid may be inserted into E. coli JM109: ATCC 53323 using electroporation.

The electroporation was carried out in accordance with a method of Dower et al. which is disclosed in Nucleic Acid Research, vol. 16, No. 13, pp. 6127–6145, 1988. The plasmid pLOD15, pLOD1 or pLOD16 was mixed with the host E. coli JM109 to be placed in an ice for one minute. The electroporation was carried out using a gene pulsar™ commercially available from BioRad under the conditions of 200 Ω, 25 μF and 12.5 kV/cm to introduce the gene. Subsequently, at a temperature of 37° C. for one hour, bacteria were cultured in a SOC medium (2% of trypton, 0.5% of yeast extract, 10 mMol of NaCl, 2.5 mMol of Kcl, 10 mMol of $MgCl_2$, 10 mMol of $MgSO_4$, and 20 mMol of glucose. After that, the bacteria were cultured in a LAH medium (1% of trypton, 0.5% of yeast extract, 0.5% of NaCl, 1.5% of agar, 0.01% of ampicillin sodium, 0.01% of ABTS, 50 mMol of lithium L-lactate, 1U/ml of Horseradish Peroxidase together with IPTG isopropyl thiogalactopyranoside, wherein temperature is 37° C. for over one night. Violet color peripheral portion means a strain which was transformed with either the plasmid pLOD15, pLOD1 or pLOD16. Single colonies were obtained by streaked onto LHA medium and cultured.

PURIFICATION OF LACTATE OXIDASE

The transformed strain was cultured at a temperature of 37° C. for 6 hours in a LA medium (1% of trypton, 0.5% of yeast extract, 0.5% of NaCl, 0.01% of ampicillin sodium, 1 mMol of IPTG) and collected by centrifugal machine. The collected bacteria were suspended in 50 mMol of potassium phosphate buffer solution with pH7.0, wherein the amount 50 mMol is seven times moisture weight of the collected bacteria. Further, 1 mg/ml of lysozyme was added. A slow agitation was made at a room temperature for 2 hours. The cell-suspension liquid was subjected to a sonication treatment using VP-60 commercially available from Titech in ice. Phenylmethyl-sulfonylfluoride and ethylene ediaminetetra acetic acid disodium salt of Wako Pure Chemical Industries Ltd, were added so that the final concentration become 1 mMol. Cell homogenate was removed. Then a slow agitation was made in ice to add ammonium sulfate in 0.31 g/ml of sampling solution to obtain 50% saturation. A further agitation was made for 30 minutes in ice and then centrifuged to be precipitated. Ammonium sulfate was further added to supernatant to obtain 80% saturation. The above processes were repeated to collect precipitate.

The obtained precipitate was dissolved in a potassium phosphate buffer solution (50 mMol of potassium phosphate and 100 mMol of Kcl at pH7.0) and then eluted using prepackaged column of Sepharose G-25 commercially available from Pharmacia Co., Ltd.

The eluted solution was equilibrated using potassiumphosphate buffer solution and then exposed to a column which is filled with an anion exchange resin such as Q-Sepharose FF. commercially available. When no absorption to a light of 280 nm wavelength by the elution solution was observed, a salt gradient is formed for elution by an elution buffer solution (50 mMol of potassiumphosphate and 500 mMol of Kcl at pH7.0) Active fractions were collected and concentrated to be equilibrated to thereby form a super dex which was used for gel filtration to thereby obtain the purified lactate oxidase.

MEASUREMENT OF ACTIVITY OF LACTATE OXIDASE

Figure 9:
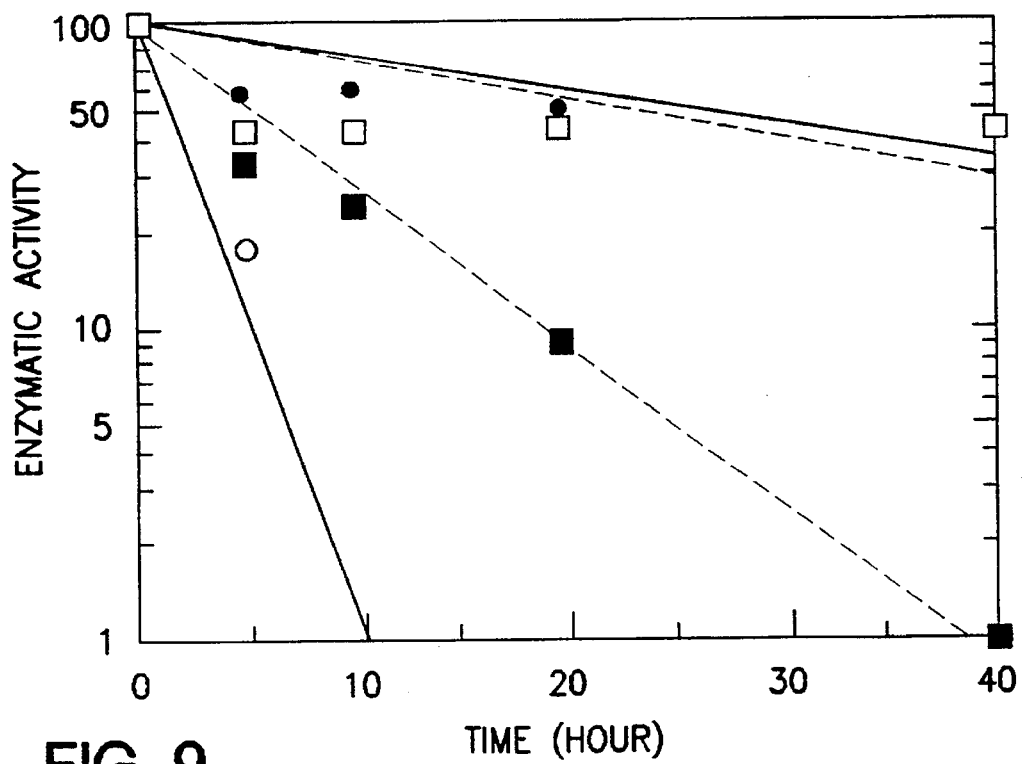
FIG. 9 is a diagram illustrative of variations in thermal stabilities over times of novel lactate oxidases (LOD15, LOD1, LOD16) of the present invention and the conventional lactate obtained from Aerococcus.

The activity of the purified lactate oxidase was measured in accordance with a method disclosed in B. B. R. C. Ducan et al. vol. 164,No. 2 pp. 919–926, 1989. 2.7 ml of pure water was added and mixed with 120 μl of HEPES buffer solution (1M, pH7.3), 30 μl of L-lactate lithium acid (96 mg/ml), 30 μl of 4-aminoantipyrin (30 mg/ml), 30 μl of phenol (31 mg/ml) and 60 μl of horseradish peroxydase (100U/ml) to be contained in a cuvette having an optical pass length. 60 μl of a lactate oxidase solution was added and agitated for subsequent measurement of variations in absorbance versus time at a wavelength of 500 nanometers by using absorptiometer UV-360 commercially available from Shimazu. 20 μg/ml of the lactate oxidase is dissolved in the potassiumphosphate buffer solution. The lactate oxidase solution was placed in a bath kept at a temperature of 65° C. for 5, 10, 20 or 40 minutes and then placed in ice to measure the enzymatic activity. As a comparative example, the enzymatic activity of the lactate oxidase obtained from Aerococcus, which is disclosed in the Japanese Patent Publication No. 59-10190. FIGS. 8 and 9 illustrate variations in enzymatic activities over times of the novel lactate oxidase according to the present invention and the conventional lactate oxidase obtained from Aerococcus. From FIGS. 8 and 9, it is apparent that the novel lactate oxidases (LOD15, LOD1, LOD16) show improved thermal stabilities clearly higher than that of the conventional lactate oxidase.

What is claimed is:

1. A mutant lactate oxidase (LOD 15) which catalyzes the oxidation of lactic acid by molecular oxygen to produce pyruvic acid, having the amino acid sequence of SEQ ID NO:2.

2. A mutant lactate oxidase (LOD 1) which catalyzes the oxidation of lactic acid by molecular oxygen to produce pyruvic acid, having the amino acid sequence of SEQ ID NO:4.

3. A mutant lactate oxidase (LOD 16) which catalyzes the oxidation of lactic acid by molecular oxygen to produce pyruvic acid, having the amino acid sequence of SEQ ID NO:6.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1122 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: CDS
        ( B ) LOCATION: 1..1122

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AAT | AAC | AAT | GAC | ATT | GAA | TAT | AAT | GCA | CCT | AGT | GAA | ATC | AAG | TAC | 48 |
| Met | Asn | Asn | Asn | Asp | Ile | Glu | Tyr | Asn | Ala | Pro | Ser | Glu | Ile | Lys | Tyr | |
| 1 | | | | 5 | | | | | 10 | | | | | 15 | | |
| ATT | GAT | GTT | GTC | AAT | ACT | TAC | GAC | TTA | GAA | GAA | GAA | GCA | AGT | AAA | GTG | 96 |
| Ile | Asp | Val | Val | Asn | Thr | Tyr | Asp | Leu | Glu | Glu | Glu | Ala | Ser | Lys | Val | |
| | | | 20 | | | | | 25 | | | | | 30 | | | |
| GTA | CCA | CAT | GGT | GGT | TTT | AAC | TAT | ATT | GCT | GGT | GCA | TCT | GGT | GAT | GAG | 144 |
| Val | Pro | His | Gly | Gly | Phe | Asn | Tyr | Ile | Ala | Gly | Ala | Ser | Gly | Asp | Glu | |
| | | 35 | | | | | 40 | | | | | 45 | | | | |
| TGG | ACT | AAA | CGC | GCT | AAT | GAC | CGT | GCT | TGG | AAA | CAT | AAA | TTA | CTA | TAC | 192 |
| Trp | Thr | Lys | Arg | Ala | Asn | Asp | Arg | Ala | Trp | Lys | His | Lys | Leu | Leu | Tyr | |
| | 50 | | | | | 55 | | | | | 60 | | | | | |
| CCA | CGT | CTA | GCG | CAA | GAT | GTT | GAA | GCG | CCC | GAT | ACA | AGT | ACT | GAA | ATT | 240 |
| Pro | Arg | Leu | Ala | Gln | Asp | Val | Glu | Ala | Pro | Asp | Thr | Ser | Thr | Glu | Ile | |
| 65 | | | | | 70 | | | | | 75 | | | | | 80 | |
| TTA | GGT | CAT | AAA | ATT | AAA | GCC | CCA | TTC | ATC | ATG | GCA | CCA | ATT | GCT | GCA | 288 |
| Leu | Gly | His | Lys | Ile | Lys | Ala | Pro | Phe | Ile | Met | Ala | Pro | Ile | Ala | Ala | |
| | | | | 85 | | | | | 90 | | | | | 95 | | |
| CAT | GGT | TTA | GCC | CAC | ACT | ACT | AAA | GAA | GCT | GGT | ACT | GCA | CGT | GCA | GTT | 336 |
| His | Gly | Leu | Ala | His | Thr | Thr | Lys | Glu | Ala | Gly | Thr | Ala | Arg | Ala | Val | |
| | | | 100 | | | | | 105 | | | | | 110 | | | |
| TCA | GAA | TTT | GGT | ACA | ATT | ATG | TCC | ATC | TCA | GCT | TAT | TCT | GGT | GCA | ACA | 384 |
| Ser | Glu | Phe | Gly | Thr | Ile | Met | Ser | Ile | Ser | Ala | Tyr | Ser | Gly | Ala | Thr | |
| | | 115 | | | | | 120 | | | | | 125 | | | | |
| TTT | GAA | GAA | ATT | TCT | GAA | GGC | TTA | AAT | GGC | GGA | CCC | CGT | TGG | TTC | CAA | 432 |
| Phe | Glu | Glu | Ile | Ser | Glu | Gly | Leu | Asn | Gly | Gly | Pro | Arg | Trp | Phe | Gln | |
| | 130 | | | | | 135 | | | | | 140 | | | | | |
| ATC | TAT | ATG | GCT | AAA | GAT | GAC | CAA | CAA | AAC | CGT | GAT | ATC | TTA | GAC | GAA | 480 |
| Ile | Tyr | Met | Ala | Lys | Asp | Asp | Gln | Gln | Asn | Arg | Asp | Ile | Leu | Asp | Glu | |
| 145 | | | | | 150 | | | | | 155 | | | | | 160 | |
| GCT | AAA | TCT | GAT | GGT | GCA | ACT | GCT | ATC | ATC | CTT | ACA | GCT | GAC | TCA | ACT | 528 |
| Ala | Lys | Ser | Asp | Gly | Ala | Thr | Ala | Ile | Ile | Leu | Thr | Ala | Asp | Ser | Thr | |
| | | | | 165 | | | | | 170 | | | | | 175 | | |
| GTT | TCT | GGA | AAC | CGT | GAC | CGT | GAT | GTG | AAG | AAT | AAA | TTC | GTT | TAC | CCA | 576 |
| Val | Ser | Gly | Asn | Arg | Asp | Arg | Asp | Val | Lys | Asn | Lys | Phe | Val | Tyr | Pro | |
| | | | 180 | | | | | 185 | | | | | 190 | | | |
| TTT | GGT | ATG | CCA | ATT | GTT | CAA | CGT | TAC | TTA | CGT | GGT | ACA | GCA | GAA | GGT | 624 |
| Phe | Gly | Met | Pro | Ile | Val | Gln | Arg | Tyr | Leu | Arg | Gly | Thr | Ala | Glu | Gly | |
| | | 195 | | | | | 200 | | | | | 205 | | | | |
| ATG | TCA | TTA | GAC | AAT | ATC | TAC | GGT | GCT | TCA | AAA | CAA | AAA | ATC | TCA | CCA | 672 |
| Met | Ser | Leu | Asp | Asn | Ile | Tyr | Gly | Ala | Ser | Lys | Gln | Lys | Ile | Ser | Pro | |
| | 210 | | | | | 215 | | | | | 220 | | | | | |
| AGA | GAT | ATT | GAG | GAA | ATC | GCC | GCT | CAT | TCT | GGA | TTA | CCA | GTA | TTC | GTT | 720 |
| Arg | Asp | Ile | Glu | Glu | Ile | Ala | Ala | His | Ser | Gly | Leu | Pro | Val | Phe | Val | |
| 225 | | | | | 230 | | | | | 235 | | | | | 240 | |
| AAA | GGT | ATT | CAA | CAC | CCA | GAA | GAT | GCA | GAT | ATG | GCA | ATC | AAA | GCT | GGT | 768 |
| Lys | Gly | Ile | Gln | His | Pro | Glu | Asp | Ala | Asp | Met | Ala | Ile | Lys | Ala | Gly | |

```
                              245                        250                         255
GCA  TCA  GGT  ATC  TGG  GTA  TCT  AAC  CAC  GGT  GCT  CGT  CAA  CTA  TAT  GAA        816
Ala  Ser  Gly  Ile  Trp  Val  Ser  Asn  His  Gly  Ala  Arg  Gln  Leu  Tyr  Glu
               260                      265                     270

GCT  CCA  GGT  TCA  TTT  GAC  ACC  CTT  CCA  GCT  ATT  GCT  GAA  CGT  GTA  AAC        864
Ala  Pro  Gly  Ser  Phe  Asp  Thr  Leu  Pro  Ala  Ile  Ala  Glu  Arg  Val  Asn
               275                      280                     285

AAA  CGT  GTA  CCA  ATC  GTC  TTT  GAT  TCA  GGT  GTA  CGT  CGT  GGT  GAA  CAC        912
Lys  Arg  Val  Pro  Ile  Val  Phe  Asp  Ser  Gly  Val  Arg  Arg  Gly  Glu  His
          290                      295                     300

GTT  GCC  AAA  GCG  CTA  GCT  TCA  GGG  GCA  GAC  GTT  GTT  GCT  TTA  GGA  CGC        960
Val  Ala  Lys  Ala  Leu  Ala  Ser  Gly  Ala  Asp  Val  Val  Ala  Leu  Gly  Arg
305                      310                      315                     320

CCA  GTC  TTA  TTT  GGT  TTA  GCT  TTA  GGT  GGC  TGG  CAA  GGT  GCT  TAC  TCA       1008
Pro  Val  Leu  Phe  Gly  Leu  Ala  Leu  Gly  Gly  Trp  Gln  Gly  Ala  Tyr  Ser
               325                      330                     335

GTA  CTT  GAC  TAC  TTC  CAA  AAA  GAC  TTA  ACA  CGC  GTA  ATG  CAA  TTA  ACA       1056
Val  Leu  Asp  Tyr  Phe  Gln  Lys  Asp  Leu  Thr  Arg  Val  Met  Gln  Leu  Thr
               340                      345                     350

GGT  TCA  CAA  AAT  GTG  GAA  GAC  TTG  AAG  GGT  CTA  GAT  TTA  TTC  GAT  AAC       1104
Gly  Ser  Gln  Asn  Val  Glu  Asp  Leu  Lys  Gly  Leu  Asp  Leu  Phe  Asp  Asn
          355                      360                     365

CCA  TAC  GGT  TAT  GAA  TAC                                                         1122
Pro  Tyr  Gly  Tyr  Glu  Tyr
370
```

( 2 ) INFORMATION FOR SEQ ID NO:2:

( i ) SEQUENCE CHARACTERISTICS:
        ( A ) LENGTH: 374 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Asn  Asn  Asp  Ile  Glu  Tyr  Asn  Ala  Pro  Ser  Glu  Ile  Lys  Tyr
 1                  5                    10                      15

Ile  Asp  Val  Val  Asn  Thr  Tyr  Asp  Leu  Glu  Glu  Ala  Ser  Lys  Val
               20                    25                      30

Val  Pro  His  Gly  Gly  Phe  Asn  Tyr  Ile  Ala  Gly  Ala  Ser  Gly  Asp  Glu
          35                    40                      45

Trp  Thr  Lys  Arg  Ala  Asn  Asp  Arg  Ala  Trp  Lys  His  Lys  Leu  Leu  Tyr
     50                    55                      60

Pro  Arg  Leu  Ala  Gln  Asp  Val  Glu  Ala  Pro  Asp  Thr  Ser  Thr  Glu  Ile
65                    70                      75                      80

Leu  Gly  His  Lys  Ile  Lys  Ala  Pro  Phe  Ile  Met  Ala  Pro  Ile  Ala  Ala
               85                    90                      95

His  Gly  Leu  Ala  His  Thr  Thr  Lys  Glu  Ala  Gly  Thr  Ala  Arg  Ala  Val
               100                   105                     110

Ser  Glu  Phe  Gly  Thr  Ile  Met  Ser  Ile  Ser  Ala  Tyr  Ser  Gly  Ala  Thr
               115                   120                     125

Phe  Glu  Glu  Ile  Ser  Glu  Gly  Leu  Asn  Gly  Gly  Pro  Arg  Trp  Phe  Gln
     130                   135                     140

Ile  Tyr  Met  Ala  Lys  Asp  Gln  Gln  Asn  Arg  Asp  Ile  Leu  Asp  Glu
145                   150                     155                     160

Ala  Lys  Ser  Asp  Gly  Ala  Thr  Ala  Ile  Ile  Leu  Thr  Ala  Asp  Ser  Thr
               165                   170                     175

Val  Ser  Gly  Asn  Arg  Asp  Arg  Asp  Val  Lys  Asn  Lys  Phe  Val  Tyr  Pro
```

180                              185                              190
Phe  Gly  Met  Pro  Ile  Val  Gln  Arg  Tyr  Leu  Arg  Gly  Thr  Ala  Glu  Gly
          195                      200                      205

Met  Ser  Leu  Asp  Asn  Ile  Tyr  Gly  Ala  Ser  Lys  Gln  Lys  Ile  Ser  Pro
     210                      215                      220

Arg  Asp  Ile  Glu  Glu  Ile  Ala  Ala  His  Ser  Gly  Leu  Pro  Val  Phe  Val
225                      230                      235                           240

Lys  Gly  Ile  Gln  His  Pro  Glu  Asp  Ala  Asp  Met  Ala  Ile  Lys  Ala  Gly
                    245                      250                           255

Ala  Ser  Gly  Ile  Trp  Val  Ser  Asn  His  Gly  Ala  Arg  Gln  Leu  Tyr  Glu
               260                      265                           270

Ala  Pro  Gly  Ser  Phe  Asp  Thr  Leu  Pro  Ala  Ile  Ala  Glu  Arg  Val  Asn
          275                      280                      285

Lys  Arg  Val  Pro  Ile  Val  Phe  Asp  Ser  Gly  Val  Arg  Arg  Gly  Glu  His
     290                      295                      300

Val  Ala  Lys  Ala  Leu  Ala  Ser  Gly  Ala  Asp  Val  Val  Ala  Leu  Gly  Arg
305                      310                      315                           320

Pro  Val  Leu  Phe  Gly  Leu  Ala  Leu  Gly  Gly  Trp  Gln  Gly  Ala  Tyr  Ser
                    325                      330                           335

Val  Leu  Asp  Tyr  Phe  Gln  Lys  Asp  Leu  Thr  Arg  Val  Met  Gln  Leu  Thr
               340                      345                           350

Gly  Ser  Gln  Asn  Val  Glu  Asp  Leu  Lys  Gly  Leu  Asp  Leu  Phe  Asp  Asn
          355                      360                      365

Pro  Tyr  Gly  Tyr  Glu  Tyr
          370

( 2 ) INFORMATION FOR SEQ ID NO:3:

( i ) SEQUENCE CHARACTERISTICS:
         ( A ) LENGTH: 1122 base pairs
         ( B ) TYPE: nucleic acid
         ( C ) STRANDEDNESS: single
         ( D ) TOPOLOGY: linear ( i i ) MOLECULE TYPE: other nucleic acid ( i x ) FEATURE:
         ( A ) NAME/KEY: CDS
         ( B ) LOCATION: 1..1122

( x i ) SEQUENCE DESCRIPTION: SEQ ID NO:3:

ATG  AAT  AAC  AAT  GAC  ATT  GAA  TAT  AAT  GCA  CCT  AGT  GAA  ATC  AAG  TAC        48
Met  Asn  Asn  Asn  Asp  Ile  Glu  Tyr  Asn  Ala  Pro  Ser  Glu  Ile  Lys  Tyr
 1                  5                       10                       15

ATT  GAT  GTT  GTC  AAT  ACT  TAC  GAC  TTA  GAA  GAA  GAA  GCA  AGT  AAA  GTG        96
Ile  Asp  Val  Val  Asn  Thr  Tyr  Asp  Leu  Glu  Glu  Glu  Ala  Ser  Lys  Val
               20                       25                       30

GTA  CCA  CAT  GGT  GGT  TTT  AAC  TAT  ATT  GCT  GGT  GCA  TCT  GGT  GAT  GAG       144
Val  Pro  His  Gly  Gly  Phe  Asn  Tyr  Ile  Ala  Gly  Ala  Ser  Gly  Asp  Glu
          35                       40                       45

TGG  ACT  AAA  CGC  GCT  AAT  GAC  CGT  GCT  TGG  AAA  CAT  AAA  TTA  CTA  TAC       192
Trp  Thr  Lys  Arg  Ala  Asn  Asp  Arg  Ala  Trp  Lys  His  Lys  Leu  Leu  Tyr
     50                       55                       60

CCA  CGT  CTA  GCG  CAA  GAT  GTT  GAA  GCG  CCC  GAT  ACA  AGT  ACT  GAA  ATT       240
Pro  Arg  Leu  Ala  Gln  Asp  Val  Glu  Ala  Pro  Asp  Thr  Ser  Thr  Glu  Ile
 65                      70                       75                            80

TTA  GGT  CAT  AAA  ATT  AAA  GCC  CCA  TTC  ATC  ATG  GCA  CCA  ATT  GCT  GCA       288
Leu  Gly  His  Lys  Ile  Lys  Ala  Pro  Phe  Ile  Met  Ala  Pro  Ile  Ala  Ala
                    85                       90                            95

CAT  GGT  TTA  GCC  CAC  ACT  ACT  AAA  GAA  GCT  GGT  ACT  GCA  CGT  GCA  GTT       336

| | | | | | | | | | | | | | | |
|---|---|---|---|---|---|---|---|---|---|---|---|---|---|---|
| His | Gly | Leu | Ala<br>100 | His | Thr | Thr | Lys | Glu<br>105 | Ala | Gly | Thr | Ala<br>110 | Arg | Ala | Val |

```
TCA  GAA  TTT  GGT  ACA  ATT  ATG  TCC  ATC  TCA  GCT  TAT  TCT  GGT  GCA  ACA        384
Ser  Glu  Phe  Gly  Thr  Ile  Met  Ser  Ile  Ser  Ala  Tyr  Ser  Gly  Ala  Thr
          115                      120                      125

TTT  GAA  GAA  ATT  TCT  GAA  GGC  TTA  AAT  GGC  GGA  CCC  CGT  TGG  TTC  CAA        432
Phe  Glu  Glu  Ile  Ser  Glu  Gly  Leu  Asn  Gly  Gly  Pro  Arg  Trp  Phe  Gln
     130                      135                      140

ATC  TAT  ATG  GCT  AAA  GAT  GAC  CAA  CAA  AAC  CGT  GAT  ATC  TTA  GAC  GGA        480
Ile  Tyr  Met  Ala  Lys  Asp  Asp  Gln  Gln  Asn  Arg  Asp  Ile  Leu  Asp  Gly
145                      150                      155                      160

GCT  AAA  TCT  GAT  GGT  GCA  ACT  GCT  ATC  ATC  CTT  ACA  GCT  GAC  TCA  ACT        528
Ala  Lys  Ser  Asp  Gly  Ala  Thr  Ala  Ile  Ile  Leu  Thr  Ala  Asp  Ser  Thr
                    165                      170                      175

GTT  TCT  GGA  AAC  CGT  GAC  CGT  GAT  GTG  AAG  AAT  AAA  TTC  GTT  TAC  CCA        576
Val  Ser  Gly  Asn  Arg  Asp  Arg  Asp  Val  Lys  Asn  Lys  Phe  Val  Tyr  Pro
               180                      185                      190

TTT  GGT  ATG  CCA  ATT  GTT  CAA  CGT  TAC  TTA  CGT  GGT  ACA  GCA  GAA  GGT        624
Phe  Gly  Met  Pro  Ile  Val  Gln  Arg  Tyr  Leu  Arg  Gly  Thr  Ala  Glu  Gly
          195                      200                      205

ATG  TCA  TTA  AAC  AAT  ATC  TAC  GGT  GCT  TCA  AAA  CAA  AAA  ATC  TCA  CCA        672
Met  Ser  Leu  Asn  Asn  Ile  Tyr  Gly  Ala  Ser  Lys  Gln  Lys  Ile  Ser  Pro
     210                      215                      220

AGA  GAT  ATT  GAG  GAA  ATC  GCC  GCT  CAT  TCT  GGA  TTA  CCA  GTA  TTC  GTT        720
Arg  Asp  Ile  Glu  Glu  Ile  Ala  Ala  His  Ser  Gly  Leu  Pro  Val  Phe  Val
225                      230                      235                      240

AAA  GGT  ATT  CAA  CAC  CCA  GAA  GAT  GCA  GAT  ATG  GCA  ATC  AAA  GCT  GGT        768
Lys  Gly  Ile  Gln  His  Pro  Glu  Asp  Ala  Asp  Met  Ala  Ile  Lys  Ala  Gly
                    245                      250                      255

GCA  TCA  GGT  ATC  TGG  GTA  TCT  AAC  CAC  GGT  GCT  CGT  CAA  CTA  TAT  GAA        816
Ala  Ser  Gly  Ile  Trp  Val  Ser  Asn  His  Gly  Ala  Arg  Gln  Leu  Tyr  Glu
               260                      265                      270

GCT  CCA  GGT  TCA  TTT  GAC  ACC  CTT  CCA  GCT  ATT  GCT  GAA  CGT  GTA  AAC        864
Ala  Pro  Gly  Ser  Phe  Asp  Thr  Leu  Pro  Ala  Ile  Ala  Glu  Arg  Val  Asn
          275                      280                      285

AAA  CGT  GTA  CCA  ATC  GTC  TTT  GAT  TCA  GGT  GTA  CGT  CGT  GGT  GAA  CAC        912
Lys  Arg  Val  Pro  Ile  Val  Phe  Asp  Ser  Gly  Val  Arg  Arg  Gly  Glu  His
     290                      295                      300

GTT  GCC  AAA  GCG  CTA  GCT  TCA  GGG  GCA  GAC  GTT  GTT  GCT  TTA  GGA  CGC        960
Val  Ala  Lys  Ala  Leu  Ala  Ser  Gly  Ala  Asp  Val  Val  Ala  Leu  Gly  Arg
305                      310                      315                      320

CCA  GTC  TTA  TTT  GGT  TTA  GCT  TTA  GGT  GGC  TGG  CAA  GGT  GCT  TAC  TCA       1008
Pro  Val  Leu  Phe  Gly  Leu  Ala  Leu  Gly  Gly  Trp  Gln  Gly  Ala  Tyr  Ser
                    325                      330                      335

GTA  CTT  GAC  TAC  TTC  CAA  AAA  GAC  TTA  ACA  CGC  GTA  ATG  CAA  TTA  ACA       1056
Val  Leu  Asp  Tyr  Phe  Gln  Lys  Asp  Leu  Thr  Arg  Val  Met  Gln  Leu  Thr
               340                      345                      350

GGT  TCA  CAA  AAT  GTG  GAA  GAC  TTG  AAG  GGT  CTA  GAT  TTA  TTC  GAT  AAC       1104
Gly  Ser  Gln  Asn  Val  Glu  Asp  Leu  Lys  Gly  Leu  Asp  Leu  Phe  Asp  Asn
          355                      360                      365

CCA  TAC  GGT  TAT  GAA  TAC                                                         1122
Pro  Tyr  Gly  Tyr  Glu  Tyr
370
```

( 2 ) INFORMATION FOR SEQ ID NO:4:

( i ) SEQUENCE CHARACTERISTICS:
        ( A ) LENGTH: 374 amino acids
        ( B ) TYPE: amino acid
        ( D ) TOPOLOGY: linear ( i i ) MOLECULE TYPE: protein (xi) SEQUENCE DESCRIPTION: SEQ ID NO:4:

| Met | Asn | Asn | Asn | Asp | Ile | Glu | Tyr | Asn | Ala | Pro | Ser | Glu | Ile | Lys | Tyr |
| 1 | | | | 5 | | | | | 10 | | | | | 15 | |

| Ile | Asp | Val | Val | Asn | Thr | Tyr | Asp | Leu | Glu | Glu | Glu | Ala | Ser | Lys | Val |
| | | | 20 | | | | | 25 | | | | | 30 | | |

| Val | Pro | His | Gly | Gly | Phe | Asn | Tyr | Ile | Ala | Gly | Ala | Ser | Gly | Asp | Glu |
| | | 35 | | | | | 40 | | | | | 45 | | | |

| Trp | Thr | Lys | Arg | Ala | Asn | Asp | Arg | Ala | Trp | Lys | His | Lys | Leu | Leu | Tyr |
| | 50 | | | | | 55 | | | | | 60 | | | | |

| Pro | Arg | Leu | Ala | Gln | Asp | Val | Glu | Ala | Pro | Asp | Thr | Ser | Thr | Glu | Ile |
| 65 | | | | | 70 | | | | | 75 | | | | | 80 |

| Leu | Gly | His | Lys | Ile | Lys | Ala | Pro | Phe | Ile | Met | Ala | Pro | Ile | Ala | Ala |
| | | | | 85 | | | | | 90 | | | | | 95 | |

| His | Gly | Leu | Ala | His | Thr | Thr | Lys | Glu | Ala | Gly | Thr | Ala | Arg | Ala | Val |
| | | | 100 | | | | | 105 | | | | | 110 | | |

| Ser | Glu | Phe | Gly | Thr | Ile | Met | Ser | Ile | Ser | Ala | Tyr | Ser | Gly | Ala | Thr |
| | | 115 | | | | | 120 | | | | | 125 | | | |

| Phe | Glu | Glu | Ile | Ser | Glu | Gly | Leu | Asn | Gly | Gly | Pro | Arg | Trp | Phe | Gln |
| | 130 | | | | | 135 | | | | | 140 | | | | |

| Ile | Tyr | Met | Ala | Lys | Asp | Asp | Gln | Gln | Asn | Arg | Asp | Ile | Leu | Asp | Gly |
| 145 | | | | | 150 | | | | | 155 | | | | | 160 |

| Ala | Lys | Ser | Asp | Gly | Ala | Thr | Ala | Ile | Ile | Leu | Thr | Ala | Asp | Ser | Thr |
| | | | | 165 | | | | | 170 | | | | | 175 | |

| Val | Ser | Gly | Asn | Arg | Asp | Arg | Asp | Val | Lys | Asn | Lys | Phe | Val | Tyr | Pro |
| | | | 180 | | | | | 185 | | | | | 190 | | |

| Phe | Gly | Met | Pro | Ile | Val | Gln | Arg | Tyr | Leu | Arg | Gly | Thr | Ala | Glu | Gly |
| | | 195 | | | | | 200 | | | | | 205 | | | |

| Met | Ser | Leu | Asn | Asn | Ile | Tyr | Gly | Ala | Ser | Lys | Gln | Lys | Ile | Ser | Pro |
| 210 | | | | | 215 | | | | | 220 | | | | | |

| Arg | Asp | Ile | Glu | Glu | Ile | Ala | Ala | His | Ser | Gly | Leu | Pro | Val | Phe | Val |
| 225 | | | | | 230 | | | | | 235 | | | | | 240 |

| Lys | Gly | Ile | Gln | His | Pro | Glu | Asp | Ala | Asp | Met | Ala | Ile | Lys | Ala | Gly |
| | | | | 245 | | | | | 250 | | | | | 255 | |

| Ala | Ser | Gly | Ile | Trp | Val | Ser | Asn | His | Gly | Ala | Arg | Gln | Leu | Tyr | Glu |
| | | | 260 | | | | | 265 | | | | | 270 | | |

| Ala | Pro | Gly | Ser | Phe | Asp | Thr | Leu | Pro | Ala | Ile | Ala | Glu | Arg | Val | Asn |
| | | 275 | | | | | 280 | | | | | 285 | | | |

| Lys | Arg | Val | Pro | Ile | Val | Phe | Asp | Ser | Gly | Val | Arg | Arg | Gly | Glu | His |
| | 290 | | | | | 295 | | | | | 300 | | | | |

| Val | Ala | Lys | Ala | Leu | Ala | Ser | Gly | Ala | Asp | Val | Val | Ala | Leu | Gly | Arg |
| 305 | | | | | 310 | | | | | 315 | | | | | 320 |

| Pro | Val | Leu | Phe | Gly | Leu | Ala | Leu | Gly | Gly | Trp | Gln | Gly | Ala | Tyr | Ser |
| | | | | 325 | | | | | 330 | | | | | 335 | |

| Val | Leu | Asp | Tyr | Phe | Gln | Lys | Asp | Leu | Thr | Arg | Val | Met | Gln | Leu | Thr |
| | | | 340 | | | | | 345 | | | | | 350 | | |

| Gly | Ser | Gln | Asn | Val | Glu | Asp | Leu | Lys | Gly | Leu | Asp | Leu | Phe | Asp | Asn |
| | | 355 | | | | | 360 | | | | | 365 | | | |

| Pro | Tyr | Gly | Tyr | Glu | Tyr |
| | 370 | | | | |

(2) INFORMATION FOR SEQ ID NO:5:

(i) SEQUENCE CHARACTERISTICS:
(A) LENGTH: 1122 base pairs (B) TYPE: nucleic acid
(C) STRANDEDNESS: single
(D) TOPOLOGY: linear (ii) MOLECULE TYPE: other nucleic acid (ix) FEATURE:
(A) NAME/KEY: CDS
(B) LOCATION: 1..1122

(xi) SEQUENCE DESCRIPTION: SEQ ID NO:5:

```
ATG AAT AAC AAT GAC ATT GAA TAT AAT GCA CCT AGT GAA ATC AAG TAC     48
Met Asn Asn Asn Asp Ile Glu Tyr Asn Ala Pro Ser Glu Ile Lys Tyr
 1               5                  10                  15

ATT GAT GTT GTC AAT ACT TAC GAC TTA GAA GAA GAA GCA AGT AAA GTG     96
Ile Asp Val Val Asn Thr Tyr Asp Leu Glu Glu Glu Ala Ser Lys Val
             20                  25                  30

GTA CCA CAT GGT GGT TTT AAC TAT ATT GCT GGT GCA TCT GGT GAT GAG    144
Val Pro His Gly Gly Phe Asn Tyr Ile Ala Gly Ala Ser Gly Asp Glu
         35                  40                  45

TGG ACT AAA CGC GCT AAT GAC CGT GCT TGG AAA CAT AAA TTA CTA TAC    192
Trp Thr Lys Arg Ala Asn Asp Arg Ala Trp Lys His Lys Leu Leu Tyr
     50                  55                  60

CCA CGT CTA GCG CAA GAT GTT GAA GCG CCC GAT ACA AGT ACT GAA ATT    240
Pro Arg Leu Ala Gln Asp Val Glu Ala Pro Asp Thr Ser Thr Glu Ile
 65                  70                  75                  80

TTA GGT CAT AAA ATT AAA GCC CCA TTC ATC ATG GCA CCA ATT GCT GCA    288
Leu Gly His Lys Ile Lys Ala Pro Phe Ile Met Ala Pro Ile Ala Ala
                 85                  90                  95

CAT GGT TTA GCC CAC ACT ACT AAA GAA GCT GGT ACT GCA CGT GCA GTT    336
His Gly Leu Ala His Thr Thr Lys Glu Ala Gly Thr Ala Arg Ala Val
             100                 105                 110

TCA GAA TTT GGT ACA ATT ATG TCC ATC TCA GCT TAT TCT GGT GCA ACA    384
Ser Glu Phe Gly Thr Ile Met Ser Ile Ser Ala Tyr Ser Gly Ala Thr
         115                 120                 125

TTT GAA GAA ATT TCT GAA GGC TTA AAT GGC GGA CCC CGT TGG TTC CAA    432
Phe Glu Glu Ile Ser Glu Gly Leu Asn Gly Gly Pro Arg Trp Phe Gln
     130                 135                 140

ATC TAT ATG GCT AAA GAT GAC CAA CAA AAC CGT GAT ATC TTA GAC GGA    480
Ile Tyr Met Ala Lys Asp Asp Gln Gln Asn Arg Asp Ile Leu Asp Gly
145                 150                 155                 160

GCT AAA TCT GAT GGT GCA ACT GCT ATC ATC CTT ACA GCT GAC TCA ACT    528
Ala Lys Ser Asp Gly Ala Thr Ala Ile Ile Leu Thr Ala Asp Ser Thr
                 165                 170                 175

GTT TCT GGA AAC CGT GAC CGT GAT GTG AAG AAT AAA TTC GTT TAC CCA    576
Val Ser Gly Asn Arg Asp Arg Asp Val Lys Asn Lys Phe Val Tyr Pro
             180                 185                 190

TTT GGT ATG CCA ATT GTT CAA CGT TAC TTA CGT GGT ACA GCA GAA GGT    624
Phe Gly Met Pro Ile Val Gln Arg Tyr Leu Arg Gly Thr Ala Glu Gly
         195                 200                 205

ATG TCA TTA GAC AAT ATC TAC GGT GCT TCA AAA CAA AAA ATC TCA CCA    672
Met Ser Leu Asp Asn Ile Tyr Gly Ala Ser Lys Gln Lys Ile Ser Pro
    210                 215                 220

AGA GAT ATT GAG GAA ATC GCC GCT CAT TCT GGA TTA CCA GTA TTC GTT    720
Arg Asp Ile Glu Glu Ile Ala Ala His Ser Gly Leu Pro Val Phe Val
225                 230                 235                 240

AAA GGT ATT CAA CAC CCA GAA GAT GCA GAT ATG GCA ATC AAA GCT GGT    768
Lys Gly Ile Gln His Pro Glu Asp Ala Asp Met Ala Ile Lys Ala Gly
                245                 250                 255

GCA TCA GGT ATC TGG GTA TCT AAC CAC GGT GCT CGT CAA CTA TAT GAA    816
Ala Ser Gly Ile Trp Val Ser Asn His Gly Ala Arg Gln Leu Tyr Glu
             260                 265                 270
```

| | | | | | | | | | | | | | | | | |
|---|---|---|---|---|---|---|---|---|---|---|---|---|---|---|---|---|
| GCT | CCA | GGT | TCA | TTT | GAC | ACC | CTT | CCA | GCT | ATT | GCT | GAA | CGT | GTA | AAC | 864 |
| Ala | Pro | Gly | Ser | Phe | Asp | Thr | Leu | Pro | Ala | Ile | Ala | Glu | Arg | Val | Asn | |
| | | 275 | | | | 280 | | | | | 285 | | | | | |
| AAA | CGT | GTA | CCA | ATC | GTC | TTT | GAT | TCA | GGT | GTA | CGT | CGT | GGT | GAA | CAC | 912 |
| Lys | Arg | Val | Pro | Ile | Val | Phe | Asp | Ser | Gly | Val | Arg | Arg | Gly | Glu | His | |
| | 290 | | | | | 295 | | | | 300 | | | | | | |
| GTT | GCC | AAA | GCG | CTA | GCT | TCA | GGG | GCA | GAC | GTT | GTT | GCT | TTA | GGA | CGC | 960 |
| Val | Ala | Lys | Ala | Leu | Ala | Ser | Gly | Ala | Asp | Val | Val | Ala | Leu | Gly | Arg | |
| 305 | | | | 310 | | | | | 315 | | | | | | 320 | |
| CCA | GTC | TTA | TTT | GGT | TTA | GCT | TTA | GGT | GGC | TGG | CAA | GGT | GCT | TAC | TCA | 1008 |
| Pro | Val | Leu | Phe | Gly | Leu | Ala | Leu | Gly | Gly | Trp | Gln | Gly | Ala | Tyr | Ser | |
| | | | | 325 | | | | | 330 | | | | | 335 | | |
| GTA | CTT | GAC | TAC | TTC | CAA | AAA | GAC | TTA | ACA | CGC | GTA | ATG | CAA | TTA | ACA | 1056 |
| Val | Leu | Asp | Tyr | Phe | Gln | Lys | Asp | Leu | Thr | Arg | Val | Met | Gln | Leu | Thr | |
| | | | 340 | | | | | 345 | | | | | 350 | | | |
| GGT | TCA | CAA | AAT | GTG | GAA | GAC | TTG | AAG | GGT | CTA | GAT | TTA | TTC | GAT | AAC | 1104 |
| Gly | Ser | Gln | Asn | Val | Glu | Asp | Leu | Lys | Gly | Leu | Asp | Leu | Phe | Asp | Asn | |
| | | 355 | | | | | 360 | | | | | 365 | | | | |
| CCA | TAC | GGT | TAT | GAA | TAC | | | | | | | | | | | 1122 |
| Pro | Tyr | Gly | Tyr | Glu | Tyr | | | | | | | | | | | |
| | | 370 | | | | | | | | | | | | | | |

( 2 ) INFORMATION FOR SEQ ID NO:6:

( i ) SEQUENCE CHARACTERISTICS:
  ( A ) LENGTH: 374 amino acids
  ( B ) TYPE: amino acid
  ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Asn | Asn | Asn | Asp | Ile | Glu | Tyr | Asn | Ala | Pro | Ser | Glu | Ile | Lys | Tyr |
| 1 | | | | 5 | | | | | 10 | | | | | 15 | |
| Ile | Asp | Val | Val | Asn | Thr | Tyr | Asp | Leu | Glu | Glu | Glu | Ala | Ser | Lys | Val |
| | | | 20 | | | | | 25 | | | | | 30 | | |
| Val | Pro | His | Gly | Gly | Phe | Asn | Tyr | Ile | Ala | Gly | Ala | Ser | Gly | Asp | Glu |
| | | 35 | | | | 40 | | | | | 45 | | | | |
| Trp | Thr | Lys | Arg | Ala | Asn | Asp | Arg | Ala | Trp | Lys | His | Lys | Leu | Leu | Tyr |
| 50 | | | | | 55 | | | | | 60 | | | | | |
| Pro | Arg | Leu | Ala | Gln | Asp | Val | Glu | Ala | Pro | Asp | Thr | Ser | Thr | Glu | Ile |
| 65 | | | | 70 | | | | | 75 | | | | | 80 | |
| Leu | Gly | His | Lys | Ile | Lys | Ala | Pro | Phe | Ile | Met | Ala | Pro | Ile | Ala | Ala |
| | | | 85 | | | | | 90 | | | | | 95 | | |
| His | Gly | Leu | Ala | His | Thr | Thr | Lys | Glu | Ala | Gly | Thr | Ala | Arg | Ala | Val |
| | | | 100 | | | | 105 | | | | | 110 | | | |
| Ser | Glu | Phe | Gly | Thr | Ile | Met | Ser | Ile | Ser | Ala | Tyr | Ser | Gly | Ala | Thr |
| | | | 115 | | | | 120 | | | | | 125 | | | |
| Phe | Glu | Glu | Ile | Ser | Glu | Gly | Leu | Asn | Gly | Gly | Pro | Arg | Trp | Phe | Gln |
| | 130 | | | | | 135 | | | | | 140 | | | | |
| Ile | Tyr | Met | Ala | Lys | Asp | Asp | Gln | Gln | Asn | Arg | Asp | Ile | Leu | Asp | Gly |
| 145 | | | | | 150 | | | | | 155 | | | | | 160 |
| Ala | Lys | Ser | Asp | Gly | Ala | Thr | Ala | Ile | Ile | Leu | Thr | Ala | Asp | Ser | Thr |
| | | | | 165 | | | | | 170 | | | | | 175 | |
| Val | Ser | Gly | Asn | Arg | Asp | Arg | Asp | Val | Lys | Asn | Lys | Phe | Val | Tyr | Pro |
| | | | 180 | | | | | 185 | | | | | 190 | | |
| Phe | Gly | Met | Pro | Ile | Val | Gln | Arg | Tyr | Leu | Arg | Gly | Thr | Ala | Glu | Gly |
| | | 195 | | | | | 200 | | | | | 205 | | | |
| Met | Ser | Leu | Asp | Asn | Ile | Tyr | Gly | Ala | Ser | Lys | Gln | Lys | Ile | Ser | Pro |

```
                        210                           215                         220
Arg  Asp  Ile  Glu  Glu  Ile  Ala  Ala  His  Ser  Gly  Leu  Pro  Val  Phe  Val
225                      230                         235                         240

Lys  Gly  Ile  Gln  His  Pro  Glu  Asp  Ala  Asp  Met  Ala  Ile  Lys  Ala  Gly
                    245                        250                     255

Ala  Ser  Gly  Ile  Trp  Val  Ser  Asn  His  Gly  Ala  Arg  Gln  Leu  Tyr  Glu
               260                      265                    270

Ala  Pro  Gly  Ser  Phe  Asp  Thr  Leu  Pro  Ala  Ile  Ala  Glu  Arg  Val  Asn
          275                      280                    285

Lys  Arg  Val  Pro  Ile  Val  Phe  Asp  Ser  Gly  Val  Arg  Arg  Gly  Glu  His
     290                      295                    300

Val  Ala  Lys  Ala  Leu  Ala  Ser  Gly  Ala  Asp  Val  Val  Ala  Leu  Gly  Arg
305                      310                     315                          320

Pro  Val  Leu  Phe  Gly  Leu  Ala  Leu  Gly  Gly  Trp  Gln  Gly  Ala  Tyr  Ser
                325                     330                          335

Val  Leu  Asp  Tyr  Phe  Gln  Lys  Asp  Leu  Thr  Arg  Val  Met  Gln  Leu  Thr
               340                     345                     350

Gly  Ser  Gln  Asn  Val  Glu  Asp  Leu  Lys  Gly  Leu  Asp  Leu  Phe  Asp  Asn
          355                      360                     365

Pro  Tyr  Gly  Tyr  Glu  Tyr
     370
```